US008828902B2

(12) United States Patent
Ramarao et al.

(10) Patent No.: US 8,828,902 B2

(45) Date of Patent: Sep. 9, 2014

(54) MICROENCAPSULATED CATALYST METHODS OF PREPARATION AND METHOD OF USE THEREOF

(75) Inventors: Chandrashekar Ramarao, Hyderabad (IN); David Joszef Tapolczay, Redbourn (GB); Ian Malcolm Shirley, Bracknell (GB); Stephen Christopher Smith, Bracknell (GB); Steven Victor Ley, Cambridge (GB)

(73) Assignee: Reaxa Limited, Manchester (GB)

( * ) Notice: Subject to any disclaimer, the term of this patent is extended or adjusted under 35 U.S.C. 154(b) by 318 days.

(21) Appl. No.: 10/483,245

(22) PCT Filed: Jul. 9, 2002

(86) PCT No.: PCT/GB02/03135

§ 371 (c)(1), (2), (4) Date: Jul. 12, 2004

(87) PCT Pub. No.: WO03/006151

PCT Pub. Date: Jan. 23, 2003

(65) Prior Publication Data

US 2004/0254066 A1 Dec. 16, 2004

(30) Foreign Application Priority Data

Jul. 12, 2001 (GB) .................................. 0117037.2
Feb. 22, 2002 (GB) .................................. 0204158.0

(51) Int. Cl.

| | |
|---|---|
| ***B01J 31/00*** | (2006.01) |
| ***C07C 209/36*** | (2006.01) |
| ***C07C 5/08*** | (2006.01) |
| ***C07C 45/62*** | (2006.01) |
| ***C07C 45/68*** | (2006.01) |
| ***C07C 201/12*** | (2006.01) |
| ***B01J 31/04*** | (2006.01) |
| ***C07C 17/263*** | (2006.01) |
| ***C07C 41/26*** | (2006.01) |
| ***C07C 67/31*** | (2006.01) |
| ***C07B 37/04*** | (2006.01) |
| ***C07C 67/36*** | (2006.01) |
| ***B01J 13/18*** | (2006.01) |
| ***C07C 67/343*** | (2006.01) |
| ***C07C 45/30*** | (2006.01) |
| ***C07C 41/30*** | (2006.01) |
| ***C07C 253/30*** | (2006.01) |
| ***C07C 29/48*** | (2006.01) |
| ***C07C 29/17*** | (2006.01) |
| ***C07C 5/03*** | (2006.01) |
| ***B01J 31/06*** | (2006.01) |
| ***C07C 209/52*** | (2006.01) |
| *B01J 35/00* | (2006.01) |
| *B01J 31/28* | (2006.01) |
| *B01J 37/02* | (2006.01) |
| *B01J 31/18* | (2006.01) |
| *B01J 31/16* | (2006.01) |
| *B01J 31/24* | (2006.01) |

(52) U.S. Cl.

CPC ............ *B01J 31/04* (2013.01); *C07B 2200/07* (2013.01); *C07C 2523/44* (2013.01); *C07C 209/36* (2013.01); *B01J 35/0013* (2013.01); *C07C 2101/14* (2013.01); *B01J 31/28* (2013.01); *C07C 5/08* (2013.01); *C07C 45/62* (2013.01); *B01J 37/0219* (2013.01); *B01J 31/1805* (2013.01); *C07C 45/68* (2013.01); *C07C 201/12* (2013.01); *C07C 17/263* (2013.01); *C07C 41/26* (2013.01); *B01J 2231/643* (2013.01); *B01J 31/165* (2013.01); *C07C 67/31* (2013.01); *C07B 37/04* (2013.01); *C07C 67/36* (2013.01); *B01J 13/18* (2013.01); *C07C 67/343* (2013.01); *B01J 2231/4261* (2013.01); *C07C 45/30* (2013.01); *B01J 2231/4211* (2013.01); *C07C 41/30* (2013.01); *C07C 253/30* (2013.01); *C07C 29/48* (2013.01); *B01J 2231/341* (2013.01); *B01J 31/24* (2013.01); *C07C 29/17* (2013.01); *C07C 5/03* (2013.01); *B01J 2231/645* (2013.01); *B01J 2231/4255* (2013.01); *B01J 2231/32* (2013.01); *B01J 31/06* (2013.01); *B01J 2531/82* (2013.01); *C07C 209/52* (2013.01)

USPC ............ 502/159; 558/388; 568/643; 570/142

(58) Field of Classification Search

USPC ......... 568/350, 434, 585, 642, 643, 811, 807, 568/852; 502/150, 152, 527.24; 560/103, 560/104, 105; 564/422, 415; 585/250, 388, 585/400

See application file for complete search history.

(56) References Cited

U.S. PATENT DOCUMENTS 3,954,666 A 5/1976 Marquisee et al. ........... 252/430

(Continued)

FOREIGN PATENT DOCUMENTS

EP 0 366 390 A2 5/1990

(Continued)

OTHER PUBLICATIONS

Satoshi Nagayama, et al., "Miroencapsulated Osmium Tetraoxide. A New Recoverable and Reusable Polymer-Supported Osmium Catalyst for Dihydroxylon of Olefins" Journal of Organic Chemistry, vol. 63, No. 18, pp. 6094-6095, 1998.

(Continued)

*Primary Examiner* — Rosalynd Keys

(74) *Attorney, Agent, or Firm* — Alan W. Steele; Foley Hoag LLP

(57) ABSTRACT

A microencapsulated catalyst is prepared by dissolving or dispersing a catalyst in a first phase (for example an organic phase), dispersing the first phase in a second, continuous phase (for example an aqueous phase) to form an emulsion, reacting one or more microcapsule wall-forming materials at the interface between the dispersed first phase and the continuous second phase to form a microcapsule polymer shell encapsulating the dispersed first phase core and optionally recovering the microcapsules from the continuous phase. The catalyst is preferably a transition metal catalyst and the encapsulated catalyst may be used for conventional catalysed reactions. The encapsulated catalyst may recovered from the reaction medium and re-cycled.

18 Claims, 1 Drawing Sheet

(56) References Cited

U.S. PATENT DOCUMENTS

| | | | | |
|---|---|---|---|---|
| 4,285,720 | A | 8/1981 | Scher | 71/88 |
| 4,421,660 | A | 12/1983 | Solc nee Hajna | 252/62.54 |
| 4,564,479 | A * | 1/1986 | Spencer | 558/371 |
| 4,871,855 | A | 10/1989 | Marko et al. | 546/134 |
| 4,956,129 | A | 9/1990 | Scher et al. | 264/4.7 |
| 5,008,457 | A | 4/1991 | Burk | 568/12 |
| 5,260,461 | A | 11/1993 | Hartung et al. | 549/447 |
| 5,332,584 | A | 7/1994 | Scher et al. | 424/408 |
| 5,489,682 | A | 2/1996 | Buchwald et al. | 544/106 |
| 5,637,739 | A | 6/1997 | Jacobsen et al. | 549/524 |
| 5,663,393 | A | 9/1997 | Jacobsen et al. | 556/45 |
| 5,767,304 | A | 6/1998 | Sharpless et al. | 560/27 |
| 5,859,281 | A | 1/1999 | Sharpless et al. | 560/12 |
| 5,929,232 | A | 7/1999 | Jacobsen et al. | 540/145 |
| 5,929,266 | A | 7/1999 | Jones et al. | 556/53 |
| 6,008,376 | A | 12/1999 | Sharpless et al. | 548/965 |
| 6,020,066 | A | 2/2000 | Weisser et al. | 428/402.21 |
| 6,362,357 | B1 * | 3/2002 | Nolan et al. | 558/44 |
| 2002/0045775 | A1 * | 4/2002 | Sun et al. | 558/359 |

FOREIGN PATENT DOCUMENTS

| | | | | |
|---|---|---|---|---|
| EP | 0 398 132 | A2 | 11/1990 | |
| EP | 0542133 | A1 | 5/1993 | B01J 13/18 |
| EP | 0 557 131 | A2 | 8/1993 | |
| EP | 0 612 758 | A1 | 8/1994 | |
| EP | 0 916 637 | A1 | 5/1999 | |
| EP | 0 940 170 | A2 | 9/1999 | |
| EP | 0940170 | A2 | 9/1999 | B01J 13/02 |
| EP | 1069127 | A1 | 1/2001 | C07F 5/00 |
| JP | 09-183859 | | 7/1997 | |
| JP | WO 99/41259 | | 8/1999 | |
| JP | 11-342341 | | 12/1999 | |
| JP | WO 02/04466 | | 1/2002 | |
| WO | WO 98/42643 | | 10/1998 | |
| WO | WO 00/26220 | | 5/2000 | |
| WO | WO 01/94001 | | 12/2001 | |
| WO | WO 02/10095 | | 2/2002 | |

OTHER PUBLICATIONS

Zhang et al., Journal of Polymer Science: Polymer Chemistry Edition, 21:3115-3127 (1983).

Petro et al., React. Kinet. Catal. Lett., 71(1):153-158 (2000).

Petro et al., React. Kinet. Catal. Lett., 73(1):187-197 (2001).

Patchornik et al., J. Chem. Soc., Chem. Commun, (1990) pp. 1090-1091.

Kobayashi et al., Organic Lett., 3(17): 2649-2652 (2001).

Shimofure et al., J. Microencapsulation, 18(1):13-17 (2001).

Blum et al., Chemtech, (Feb. 1999), pp. 32-38.

Nagayama et al., J. Org. Chem., 63:6094-6095 (1998).

Kobayashi et al., J. Am. Chem. Soc., 120:2985-2986 (1998).

Burgess et al., Chem. Rev., 91:1179-1191 (1991).

Pfaltz, Acc. Chem. Res., 26:339-345 (1993).

Brown et al., J. Chem. Soc., Chem. Commun., (1993), pp. 1673-1674.

Trost et al.; J. Am. Chem. Soc., 114:9327-9343 (1992).

van de Kuil et al., Organometallics, 16:4985-4994 (1997).

Cserépi-Szües et al., Chem. Commun, (1997), pp. 635-636.

Verdaguer et al., J. Am. Chem. Soc., 118:6784-6785 (1996).

O'Dell et al., J. Am. Chem. Soc., 116:3414-3423 (1994).

Huang et al., J. Am. Chem. Soc., 121:2674-2678 (1999).

Fu et al., J. Am. Chem. Soc., 115:9856-9857 (1993).

Herrmann et al., Angew. Chem. Int. Ed. Engl., 34(17):1844-1848 (1995).

Albisson et al., Chem. Commun., (998), pp. 2095-2096.

Joscelyne et al., Journal of Membrane Science, 169:107-117 (2000).

Scher et al., "Microencapsulation of Pesticides by Interfacial Polymerization Utilizing Isocyanate or Aminoplast Chemistry", Pestic. Sci., 54:394-400 (1998).

Ishida et al., "A Novel Microencapsulated Osmium Catalyst Using Cross-Linked Polystyrene as an Efficient Catalyst for Asymmetric Dihydroxylation of Olefins in Water", Adv. Synth. Catal., 347:1189-1192 (2005).

* cited by examiner

*Beckman Coulter - LS Particle Size Analyser*
| | | | |
|---|---|---|---|
| **File Name:** | Microenc.37 | **Group ID:** | Microencapsulated Catalysts |
| **Sample ID:** | NBZ2632/37 | **Operator:** | MN |
| **Run Number:** | 1 | | |
| **Comments:** | 10L run @ 240 rpm | | |
| **Optical Method:** | Fraunhofer.rfd | | |
| **LS 320** | Small Volume Module | | |
| **Start time:** | 13:40 28 Nov 2001 | **Run length:** | 60 seconds |
| **Obscuration:** | 9% | | |
| **Software:** | 3:01 | **Firmware:** | 2.02 0 |
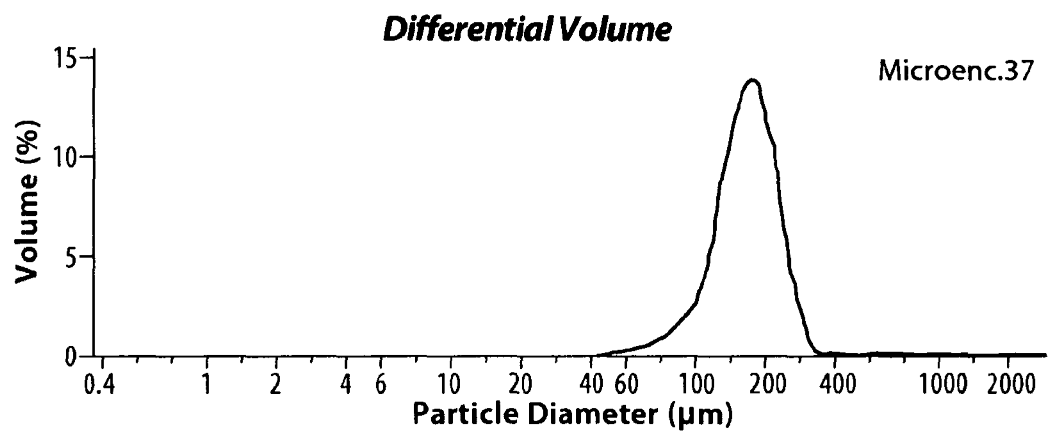

MICROENCAPSULATED CATALYST METHODS OF PREPARATION AND METHOD OF USE THEREOF

RELATED APPLICATIONS

The present application is a 371 filing based on PCT/GB02/003135 filed Jul. 9, 2002 and claims priority benefit from said PCT filing and the earlier filed UK Application No. 0117037.2, filed Jul. 12, 2001 and UK Application No. 0204158.0, filed Feb. 22, 2002.

BACKGROUND OF THE INVENTION

This invention relates to a catalyst, to a method of preparing a catalyst and in particular to a method of preparing a microencapsulated catalyst.

Catalysts, such as transition metal catalysts, are widely used in a variety of chemical reactions. Difficulties are frequently encountered however, particularly on the commercial scale, in recovering and re-using the catalyst. This not only results in potential contamination of the product but also represents a significant cost burden in terms of usage of expensive catalyst. Polymer-supported catalysts are well known but suffer from a number of disadvantages such as poor physical stability and low catalyst availability. Furthermore heterogeneous reaction systems used with polymer-supported catalysts are inherently more complex to operate on a commercial scale.

Various attempts have been made to overcome these difficulties. In EP 0940170 for example there is described a process wherein an aromatic substituted polyolefin such as polystyrene is dissolved in an organic solvent such as cyclohexane to which is added osmium tetroxide catalyst. The solution is cooled and the aromatic substituted polyolefin is precipitated, for example by the addition of methanol. The resultant product was shown to be an effective catalyst. The precipitation of the aromatic polymer however is uncontrolled and results in an amorphous and unstructured mass, monolith or matrix of solid polyolefin within which the osmium tetroxide particles are trapped. It is a further drawback of this process that the trapped catalyst system cannot subsequently be used effectively in a reaction medium in which the polymer is soluble or becomes plasticised since the free catalyst will be liberated. This therefore limits the utility of the catalyst.

SUMMARY OF THE INVENTION

According to the present invention there is provided a catalyst system comprising a catalyst microencapsulated within a permeable polymer microcapsule shell.

BRIEF DESCRIPTION OF THE DRAWING

FIG. 1 is a graph depicting a particle size trace for a Pd microcapsule batch.

DETAILED DESCRIPTION OF THE INVENTION

The term "encapsulation" has different connotations depending on the application area. Microencapsulation in the present context describes the containment of a finely divided solid or liquid in a polymeric micro-particle, where milling or grinding a larger mass has not made the micro-particle. The term 'monolithic' or 'matrix' describes a particle having a finely divided solid or liquid distributed throughout a 'solid' or amorphous polymeric bead, while the term 'reservoir' describes a particle where the finely divided solid or liquid is contained within an inner cavity bound by an integral outer polymer shell. Thus as used herein the term "microencapsulated within a permeable polymer microcapsule shell" indicates that the polymer shell containing the catalyst is itself in the form of a microcapsule, formed for example by one of the techniques described in greater detail below. A microcapsule formed by such techniques will be generally spherical or collapsed spherical and have a mean diameter of from 1 to 1000 microns, preferably from 25 to 500 microns and especially from 50 to 300 microns. The polymer microcapsule shell is permeable to the extent that the reaction medium being catalysed is capable of contacting the encapsulated catalyst.

Various processes for microencapsulating material are available. These processes can be divided into three broad categories (a) physical, (b) phase separation and (c) interfacial reaction methods. In the physical methods category, microcapsule wall material and core particles are physically brought together and the wall material flows around the core particle to form the microcapsule. In the phase separation category, microcapsules are formed by emulsifying or dispersing the core material in an immiscible continuous phase in which the wall material is dissolved and caused to physically separate from the continuous phase, such as by coacervation, and deposit around the core particles. In the interfacial reaction category, the core material is emulsified or dispersed in an immiscible continuous phase, and then an interfacial polymerization reaction is caused to take place at the surface of the core particles thereby forming microcapsules.

The above processes vary in utility. Physical methods, such as spray drying, spray chilling and humidized bed spray coating, have limited utility for the microencapsulation of products because of volatility losses and pollution control problems associated with evaporation of solvent or cooling, and because under most conditions not all of the product is encapsulated nor do all of the polymer particles contain product cores. Phase separation techniques suffer from process control and product loading limitations. It may be difficult to achieve reproducible phase separation conditions, and it may be difficult to assure that the phase-separated polymer will preferentially wet the core droplets.

Interfacial polymerisation reaction methods are therefore preferred for encapsulation of the catalyst within the polymer microcapsule shell.

Thus according to a further aspect of the present invention there is provided a catalyst system comprising a catalyst microencapsulated within a permeable polymer microcapsule shell wherein the microcapsule shell is formed by interfacial polymerisation.

According to a further aspect of the present invention there is provided a process for the preparation of a microencapsulated catalyst which comprises forming a microcapsule shell by interfacial polymerisation in the presence of a catalyst.

There are various types of interfacial polymerisation techniques but all involve reaction at the interface of a dispersed phase and a continuous phase in an emulsion system. Typically the dispersed phase is an oil phase and the continuous phase is an aqueous phase but interfacial polymerisation reactions at the interface of a continuous oil phase and a dispersed aqueous phase are also possible. Thus for example an oil or organic phase is dispersed into a continuous aqueous phase comprising water and a surface-active agent. The organic phase is dispersed as discrete droplets throughout the aqueous phase by means of emulsification, with an interface between the discrete organic phase droplets and the surrounding continuous aqueous phase solution being formed. Polymerisation at this interface forms the microcapsule shell surrounding the dispersed phase droplets.

In one type of interfacial condensation polymerisation microencapsulation process, monomers contained in the oil and aqueous phase respectively are brought together at the oil/water interface where they react by condensation to form the microcapsule wall. In another type of polymerisation reaction, the in situ interfacial condensation polymerisation reaction, all of the wall-forming monomers are contained in the oil phase. In situ condensation of the wall-forming materials and curing of the polymers at the organic-aqueous phase interface may be initiated by heating the emulsion to a temperature of between about 20° C. to about 100° C. and optionally adjusting the pH. The heating occurs for a sufficient period of time to allow substantial completion of in situ condensation of the prepolymers to convert the organic droplets to capsules consisting of solid permeable polymer shells enclosing the organic core materials.

One type of microcapsule prepared by in situ condensation and known in the art is exemplified in U.S. Pat. Nos. 4,956,129 and 5,332,584. These microcapsules, commonly termed "aminoplast" microcapsules, are prepared by the self-condensation and/or cross-linking of etherified urea-formaldehyde resins or prepolymers in which from about 50 to about 98% of the methylol groups have been etherified with a $C_4$-$C_{10}$ alcohol (preferably n-butanol). The prepolymer is added to or included in the organic phase of an oil/water emulsion. Self-condensation of the prepolymer takes place optionally under the action of heat at low pH. To form the microcapsules, the temperature of the two-phase emulsion is raised to a value of from about 20° C. to about 90° C., preferably from about 40° C. to about 90° C., most preferably from about 40° C. to about 60° C. Depending on the system, the pH value may be adjusted to an appropriate level. For the purpose of this invention a pH of about 1.5 to 3 is appropriate:

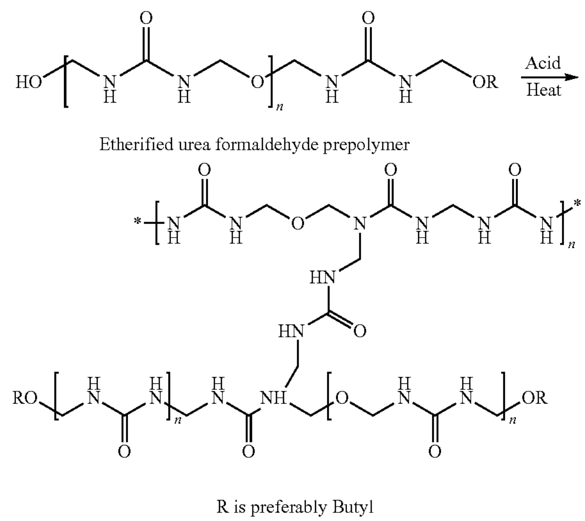

As described in U.S. Pat. No. 4,285,720 the prepolymers most suitable for use in this invention are partially etherified urea-formadehyde prepolymers with a high degree of solubility in organic phase and a low solubility in water. Etherified urea-formaldehyde prepolymers are commercially available in alcohol or in a mixture of alcohol and xylene. Examples of preferred commercially available prepolymers include the Beetle etherified urea resins manufactured by BIP (e.g. BE607, BE610, BE660, BE676) or the Dynomin N-butylated urea resins from Dyno Cyanamid (e.g. Dynomin UB-24-BX, UB-90-BX etc.).

Acid catalysts capable of enhancing the microcapsule formation can be placed in either the aqueous or the organic phase. Catalysts are generally used when the core material is too hydrophobic, since they serve to attract protons towards the organic phase. Any water soluble catalyst which has a high affinity for the organic phase can be used. Carboxylic and sulphonic acids are particularly useful.

One further type of microcapsule prepared by in situ condensation and found in the art, as exemplified in U.S. Pat. No. 4,285,720 is a polyurea microcapsule which involves the use of at least one polyisocyanate such as polymethylene polyphenyleneisocyanate (PMPPI) and/or tolylene diisocyanate (TDI) as the wall-forming material. In the creation of polyurea microcapsules, the wall-forming reaction is generally initiated by heating the emulsion to an elevated temperature at which point a proportion of the isocyanate groups are hydrolyzed at the interface to form amines, which in turn react with unhydrolyzed isocyanate groups to form the polyurea microcapsule wall. During the hydrolysis of the isocyanate monomer, carbon dioxide is liberated. The addition of no other reactant is required once the dispersion establishing droplets of the organic phase within a continuous liquid phase, i.e., aqueous phase, has been accomplished. Thereafter, and preferably with moderate agitation of the dispersion, the formation of the polyurea microcapsule can be brought about by heating the continuous liquid phase or by introducing a catalyst such as an alkyl tin or a tertiary amine capable of increasing the rate of isocyanate hydrolysis.

The organic phase thus comprises the catalyst to be encapsulated, a polyisocyanate and optionally organic solvent. The catalyst can be in a concentrated form or as a solution in a water immiscible solvent. The catalyst to be encapsulated and the polyisocyanate are typically premixed under slow agitation to obtain a homogeneous organic phase before addition to and mixing with the aqueous phase. The amount of the organic phase may vary from about 1% to about 75% by volume of the aqueous phase present in the reaction vessel. The preferred amount of organic phase is about 10 percent to about 50 percent by volume. The organic polyisocyanates used in this process includes both aromatic and aliphatic mono and poly functional isocyanates. Examples of suitable aromatic diisocyantes and other polyisocyantes include the following: 1-chloro-2,4-phenylene diisocyante, m-phenylene diisocyante (and its hydrogenated derivative), p-phenylene diisocyante (and its hydrogenated derivative), 4,4'-methylenebis (phenyl isocyanate), 2,4-tolylene diisocyanate, tolylene diisocyanate (60% 2,4-isomer, 40% 2,6-isomer), 2,6-tolylene diisocyante, 3,3'-dimethyl-4,4'-biphenylene diisocyante, 4,4'-methylenebis(2-methylphenyl isocyanate), 3,3'-dimethoxy-4,4'-biphenylene diisocyanate, 2,2',5,5'-tetramethyl-4,4'-biphenylene diisocyanate, 80% 2,4- and 20% 2,6-isomer of tolylene diisocyanate, polymethylene polyphenylisocyante (PMPPI), 1,6-hexamethylene diisocyanate, isophorone diisocyanate, tetramethylxylene diisocyanate and 1,5-naphthylene diisocyanate.

It may be desirable to use combinations of the above mentioned polyisocyantes. Preferred polyisocyantes are polymethylene polyphenylisocyante (PMPPI) and mixtures of polymethylene polyphenylisocyante (PMPPI) with tolylene diisocyanate.

One further class of polymer precursors consists of a primarily oil-soluble component and a primarily water-soluble component which react together to undergo interfacial polymerisation at a water/oil interface. Typical of such precursors are an oil-soluble isocyanate such as those listed above and a water-soluble poly amine such as ethylenediamine and/or diethylenetriamine to ensure that chain extension and/or cross-linking takes place. Cross-linking variation may be achieved by increasing the functionality of the amine. Thus for example, cross-linking is increased if ethylenediamine is replaced by a polyfunctional amine such as DETA (Diethylene triamine), TEPA (Tetraethylene pentamine) and other well established cross linking amines. Isocyanate functionality can be altered (and thus cross-linking also altered) by moving from monomeric isocyanates such as toluene diisocyanate to PMPPI. Mixtures of isocyanates, for example mixtures of tolylene diisocyanate and PMPPI, may also be used. Moreover, the chemistry may be varied from aromatic isocyanates to aliphatic isocyanates such as hexamethylenediisocyanate and isophorone diisocyanate. Further modifications can be achieved by partially reacting the (poly)isocyanate with a polyol to produce an amount of a polyurethane within the isocyanate chemistry to induce different properties to the wall chemistry. For example, suitable polyols could include simple low molecular weight aliphatic di, tri or tetraols or polymeric polyols. The polymeric polyols may be members of any class of polymeric polyols, for example: polyether, polyTHF, polycarbonates, polyesters and polyesteramides. One skilled in the art will be aware of many other chemistries available for the production of a polymeric wall about an emulsion droplet. As well as the established isocyanate/amine reaction to produce a polyurea wall chemistry, there can be employed improvements to this technology including for example that in which hydrolysis of the isocyanate is allowed to occur to an amine which can then further react internally to produce the polyurea chemistry (as described for example in U.S. Pat. No. 4,285,720). Variation in the degree of cross linking may be achieved by altering the ratio of monomeric isocyanate to polymeric isocyanate. As with the conventional isocyanate technology described above, any alternative isocyanates can be employed in this embodiment.

One skilled in the art will be aware that the various methods previously described to produce polyurea microcaps typically leave unreacted amine (normally aromatic amine) groups attached to the polymer matrix. In some cases it may be advantageous to convert such amine groups to a substantially inert functionality. Preferred are methods for the conversion of such amine groups to urea, amide or urethane groups by post reaction of the microcapsules in an organic solvent with a monoisocyanate, acid chloride or chloroformate respectively.

U.S. Pat. No. 6,020,066 (assigned to Bayer AG) discloses another process for forming microcapsules having walls of polyureas and polyiminoureas, wherein the walls are characterized in that they consist of reaction products of crosslinking agents containing $NH_2$ groups with isocyanates. The crosslinking agents necessary for wall formation include di- or polyamines, diols, polyols, polyfunctional amino alcohols, guanidine, guanidine salts, and compounds derived there from. These agents are capable of reacting with the isocyanate groups at the phase interface in order to form the wall.

The preferred materials for the microcapsule are a polyurea, formed as described in U.S. Pat. No. 4,285,720, or a urea-formaldehyde polymer as described in U.S. Pat. No. 4,956,129. Polyurea is preferred because the microcapsule is formed under very mild conditions and does not require acidic pH to promote polymerisation and so is suitable for use with an acid-sensitive catalysts. The most preferred polymer type for the microcapsule is polyurea as described in U.S. Pat. No. 4,285,720 based on the PMPPI polyisocyanate.

Whilst the scope of the present invention is not to be taken as being limited by any one particular theory, it is believed that certain microcapsule wall-forming moieties, such as for example isocyanate moieties, may provide co-ordinating functionality in respect to a transition metal catalyst. Such co-ordination may result in the possibility of stabilisation of finely dispersed or colloidal catalysts and/or the possibility of enhanced binding of the catalyst to the microcapsule polymer wall.

Certain organic or naturally occurring catalysts which act as ligands (for example tertiary amines) may interfere with reaction of the components forming the polymer microcapsule shell and it is preferred that the catalyst is an inorganic catalyst and in particular a transition metal catalyst. The term transition metal catalyst as used herein includes (a) the transition metal itself, normally in finely divided or colloidal form, (b) a complex of a transition metal with a suitable ligand or (c) a compound containing a transition metal. If desired a pre-cursor for the catalyst may be microencapsulated within the polymer microcapsule shell and subsequently converted to the catalyst, for example by heating. The term catalyst thus also includes a catalyst pre-cursor.

Microencapsulation techniques described above most commonly involve the microencapsulation of an oil phase dispersed within an aqueous continuous phase, and for such systems the catalyst is suitably capable of being suspended within the microencapsulated oil phase or more preferably is soluble in a water-immiscible organic solvent suitable for use as the dispersed phase in microencapsulation techniques. The scope of the present invention is not however restricted to the use of oil-in-water microencapsulation systems and water-soluble catalysts may be encapsulated via interfacial microencapsulation of water-in-oil emulsion systems. Water-soluble catalysts may also be encapsulated via interfacial microencapsulation of water-in-oil-in-water emulsion systems.

We have found that certain catalysts may catalyse the wall-forming reaction during interfacial polymerisation. In general it is possible to modify the microencapsulation conditions to take account of this. Some interaction, complexing or bonding between the catalyst and the polymer shell may be positively desirable since it may prevent agglomeration of finely divided or colloidal catalysts.

In some instances, the metal catalyst being encapsulated may increase the rate of the interfacial polymerisation reactions. In such cases it may be advantageous to cool one or both of the organic and continuous aqueous phases such that interfacial polymerisation is largely prevented whilst the organic phase is being dispersed. The reaction is then initiated by warming in a controlled manner once the required organic droplet size has been achieved. For example, in certain reactions the aqueous phase may be cooled to less than 10° C., typically to between 5° C. to 10° C., prior to addition of the oil phase and then when the organic phase is dispersed the aqueous phase may be heated to raise the temperature above 15° C. to initiate polymerisation.

Preferred transition metals on which the catalysts for use in the present invention may be based include platinum, palladium, osmium, ruthenium, rhodium, iridium, rhenium, scandium, cerium, samarium, yttrium, ytterbium, lutetium, cobalt, titanium, chromium, copper, iron, nickel, manganese, tin, mercury, silver, gold, zinc, vanadium, tungsten and molybdenum. Especially preferred transition metals on which the catalysts for use in the present invention may be based include palladium, osmium, ruthenium, rhodium, titanium, vanadium and chromium. Air sensitive catalysts may be handled using conventional techniques to exclude air.

An example of a water-soluble catalyst which may be encapsulated via a water-in oil emulsion microencapsulation process is scandium triflate.

Osmium in the form of osmium tetroxide is useful as a catalyst in a variety of oxidation reactions. Since it has a high vapour pressure even at room temperature and its vapour is toxic, microencapsulation of osmium tetroxide according to the present invention has the added advantage of a potential reduction in toxicity problems. Osmium tetroxide is soluble in solvents, in particular hydrocarbon solvents, which are suitable for forming the dispersed phase in a microencapsulation reaction.

Palladium in a variety of forms may be microencapsulated according to the present invention and is useful as a catalyst for a wide range of reactions. Colloidal palladium may be produced as an organic phase dispersion and is conveniently stabilised by quaternary ammonium salts such as tetra-n-octylammonium bromide. Thus for example colloidal palladium may be produced by the thermal decomposition of palladium acetate dissolved in a solvent such as tetrahydrofuran in the presence of tetra-n-octylammonium bromide as stabiliser. The tetrahydrofuran solvent is suitably removed, for example under reduced pressure, and may be replaced by a solvent which is water-immiscible and is hence more suitable for the microencapsulation process. Whilst such a colloidal suspension of palladium may be successfully microencapsulated, we have found that the stabilised palladium tends to catalyse the polymerisation reaction at the interface (probably the via octylammonium bromide acting as a ligand) and it may be necessary to adjust the microencapsulation conditions accordingly.

Alternatively palladium may be used directly in the form of palladium acetate. Thus for example palladium acetate may be suspended or more preferably dissolved in a suitable solvent such as a hydrocarbon solvent or a chlorinated hydrocarbon solvent and the resultant solution may be microencapsulated according to the present invention. Chloroform is a preferred solvent for use in the microencapsulation of palladium acetate. Whilst the scope of the present invention is not to be taken as being limited by any one particular theory, it is believed that the solubility of the catalyst in the organic phase is increased in the presence of an isocyanate microcapsule wall-forming moiety, either as a result of an increase in polarity of the organic phase or possibly via co-ordination with the metal.

According to literature sources palladium acetate decomposes to the metal under the action of heat. Catalysts of the present invention derived from palladium acetate have proved to be effective, although it is not presently known whether palladium is present in the form of the metal or remains as palladium acetate.

It is to be understood that the microencapsulated catalysts of the present invention include microencapsulated catalysts wherein the loading level of catalyst can be varied. Microencapsulated catalysts with loadings of 0.01 mmol/g to 0.6 mmol/g of catalyst are typical, especially where the loading is based on the metal content. Loadings of 0.2 mmol/g to 0.4 mmol/g are frequently favoured.

In addition to the metal catalysts and metal oxide catalysts, many additional catalysts which may be microencapsulated in accordance with the present invention will occur to those skilled in the art. Without limitation to the foregoing, the following are examples of suitable catalysts:—

Catalysts disclosed in Catalytic Asymmetric Synthesis 2nd Ed. Ed. I. Ojima Wiley-VCH including without limitation the list of chiral ligands included in the appendix thereof;

Metal diphosphine catalysts such as those disclosed in EP612758 Solvias RhJosiPhos, EP366390 Takasago RuBINAP, EP398132 Roche MeOBIPHEP, U.S. Pat. No. 5,008,457 DuPont DuPhos and PCT/GB99/03599 OxPhos;

Metal phosphine catalysts such as Wilkinson's catalysts disclosed in Chem. Rev., 1991, 91, 1179;

Metal phosphoramidate catalysts such as those disclosed in WO02/04466 DSM MonoPhos;

Metal aminophosphine catalysts such as those disclosed in A. Pfaltz Acc. Chem. Res. 1993, 26, 339, J. M. Brown, D. Hulmes, T. Layzell J. Chem. Soc. Chem. Commun. 22, 1673, 1993, and J. Am. Chem. Soc., 1992, 114, 9327;

Metal arylamine catalysts such as those disclosed in Organometallics, 1997, 16 (23), 4985-4994;

Metal diamine catalysts such as those disclosed in U.S. Pat. No. 5,663,393 Jacobsen epoxidation, U.S. Pat. No. 5,637,739 Jacobsen epoxidation, U.S. Pat. No. 5,929,232 Jacobsen epoxide resolution, U.S. Pat. No. 4,871,855 Sharpless dihydroxylation, U.S. Pat. No. 5,260,461 Sharpless dihydroxylation, U.S. Pat. No. 5,767,304 Sharpless aminohydroxylation, U.S. Pat. No. 5,859,281 Sharpless aminohydroxylation, U.S. Pat. No. 6,008,376 Sharpless aminohydroxylation and WO02/10095 for Catalytic Asymmetric Cyanohydrin;

Metal aminoalcohol catalysts such as those disclosed in WO9842643 Zeneca CATHy, and EP0916637 ERATO Noyori CTH;

Metal phosphate catalysts such as those disclosed in Cserepi-Szucs, S., Bakos, J. Chem. Soc. Chem. Commun. 1997, 635;

Metal salt catalysts such as salts of magnesium, aluminium, tin and iron for instance halide salts such as chlorides of magnesium, aluminium, tin and iron;

Metal alkoxide catalysts such as those disclosed in Verdaguer X., Lange, U. E. W., Reding, M. T., Buchwald S. L. J. Am. Chem. Soc. 1996, 118, 6784;

Metal arene catalysts such as those disclosed in U.S. Pat. No. 5,489,682 Buchwald hydrogenation, U.S. Pat. No. 5,929,266 Whitby hydrogenation;

Metal arene phosphine catalysts such as those disclosed in Ciruelos, S., Englert, E., Salzer, A., Bolm, C., Maischak, A. Organometallics 19, 2240, 2000;

Metal carbene catalysts for alkene metathesis such as those described in J. Am. Chem. Soc., 1994, 116, 3414, J. Am. Chem. Soc., 1999, 121, 2674 and J. Am. Chem. Soc. 1993, 115, 9856; and Metallocycle catalysts such as those described in Angew. Chem. 1995, 34, 1844 and Chem. Commun. 1998, 2095.

The microencapsulation of the catalyst takes place according to techniques well known in the art. Typically the catalyst is dissolved or dispersed in an oil phase which is emulsified into a continuous aqueous phase to form an emulsion which is generally stabilised by a suitable surfactant system. A wide variety of surfactants suitable for forming and stabilising such emulsions are commercially available and may be used either as the sole surfactant or in combination. The emulsion may be formed by conventional low or high-shear mixers or homogenisation systems, depending on particle size requirements. A wide range of continuous mixing techniques can also be utilised. Suitable mixers which may be employed in particular include dynamic mixers whose mixing elements contain movable pads and static mixers which utilise mixing elements without moving parts in the interior. Combinations of mixers (typically in series) may be advantageous. Examples of the types of mixer which may be employed are discussed in U.S. Pat. No. 6,271,320 which is herein incorporated by reference.

Alternatively, emulsions may be formed by membrane emulsification methods. Examples of membrane emulsification methods are reviewed in Journal of Membrane Science 169 (2000) 107-117 which is herein incorporated by reference.

Typical examples of suitable surfactants include:

a) condensates of alkyl (eg octyl, nonyl or polyaryl)phenols with ethylene oxide and optionally propylene oxide and anionic derivatives thereof such as the corresponding ether sulphates, ether carboxylates and phosphate esters;
   block copolymers of polyethylene oxide and polypropylene oxide such as the series of surfactants commercially available under the trademark PLURONIC (PLURONIC is a trademark of BASF);
b) TWEEN surfactants, a series of emulsifiers comprising a range of sorbitan esters condensed with various molar proportions of ethylene oxide;
c) condensates of $C_8$ to $C_{30}$ alkanols with from 2 to 80 molar proportions of ethylene oxide and optionally propylene oxide; and
d) polyvinyl alcohols, including the carboxylated and sulphonated products.

Furthermore, WO 01/94001 teaches that one or more wall modifying compounds (termed surface modifying agents) can, by virtue of reaction with the wall forming materials, be incorporated into the microcapsule wall to create a modified microcapsule surface with built in surfactant and/or colloid stabiliser properties. Use of such modifying compounds may enable the organic phase wall forming material to be more readily dispersed into the aqueous phase possibly without the use of additional colloid stabilisers or surfactants and/or with reduced agitation. The teaching of WO01/94001 is herein incorporated by reference. Examples of wall modifying compounds which may find particular use in the present invention include anionic groups such as sulphonate or carboxylate, non-ionic groups such as polyethylene oxide or cationic groups such as quaternary ammonium salts.

In addition the aqueous phase may contain other additives which may act as aids to the process of dispersion or the reaction process. For example, de-foamers may be added to lesson foam build up, especially foaming due to gas evolution.

A wide variety of materials suitable for use as the oil phase will occur to one skilled in the art. Examples include, diesel oil, isoparaffin, aromatic solvents, particularly alkyl substituted benzenes such as xylene or propyl benzene fractions, and mixed napthalene and alkyl napthalene fractions; mineral oils, white oil, castor oil, sunflower oil, kerosene, dialkyl amides of fatty acids, particularly the dimethyl amides of fatty acids such as caprylic acid; chlorinated aliphatic and aromatic hydrocarbons such as 1,1,1-trichloroethane and chlorobenzene, esters of glycol derivatives, such as the acetate of the n-butyl, ethyl, or methyl ether of diethylene glycol, the acetate of the methyl ether of dipropylene glycol, ketones such as isophorone and trimethylcyclohexanone (dihydroisophorone) and the acetate products such as hexyl, or heptyl acetate. Organic liquids conventionally preferred for use in microencapsulation processes are xylene, diesel oil, isoparaffins and alkyl substituted benzenes, although some variation in the solvent may be desirable to achieve sufficient solubility of the catalyst in the oil phase.

It is preferred that microencapsulation of the oil phase droplets containing the catalyst takes place by an interfacial polymerisation reaction as described above. The aqueous dispersion of microcapsules containing the catalyst may be used to catalyse a suitable reaction without further treatment. Preferably however the microcapsules containing the catalyst are removed from the aqueous phase by filtration. It is especially preferred that the recovered microcapsules are washed with water to remove any remaining surfactant system and with a solvent capable of extracting the organic phase contained within the microcapsule. Relatively volatile solvents such as halogenated hydrocarbon solvents for example chloroform are generally more readily removed by washing or under reduced pressure than are conventional microencapsulation solvents such as alky substituted benzenes. If the majority of the solvent is removed, the resultant microcapsule may in effect be a substantially solvent-free polymer bead containing the catalyst efficiently dispersed within the microcapsule polymer shell. The process of extracting the organic phase may cause the microcapsule walls to collapse inward, although the generally spherical shape will be retained. If desired the dry microcapsules may be screened to remove fines, for example particles having a diameter less than about 20 microns.

In the case of the microencapsulated palladium acetate microparticles it is preferred that the recovered water wet microcapsules are washed with copious quantities of deionised water, followed by ethanol washes and finally hexane washes. The microcapsules are then dried in a vac oven at 50° C. for approx 4 hours to give a product with greater than 98% non volatile content (by exhaustive drying).

Depending on the conditions of preparation and in particular the degree of interaction between the catalyst and the wall-forming materials, the microencapsulated catalyst of the present invention may be regarded at one extreme as a 'reservoir' in which the finely divided catalyst (either as solid or in the presence of residual solvent) is contained within an inner cavity bound by an integral outer polymer shell or at the other extreme as a solid, amorphous polymeric bead throughout which the finely divided catalyst is distributed. In practice the position is likely to be between the two extremes. Regardless of the physical form of the encapsulated catalyst of the present invention and regardless of the exact mechanism by which access of reactants to the catalyst takes place (diffusion through a permeable polymer shell or absorption into a porous polymeric bead), we have found that encapsulated catalysts of the present invention permit effective access of the reactants to the catalyst whilst presenting the catalyst in a form in which it can be recovered and if desired re-used. Furthermore, since in the preferred embodiment of the present invention the polymer shell/bead is formed in situ by controlled interfacial polymerisation (as opposed to uncontrolled deposition from an organic solution of the polymer), the microencapsulated catalyst of the present invention may be used in a wide range of organic solvent-based reactions.

The microcapsules of this invention are regarded as being insoluble in most common organic solvents by virtue of the fact that they are highly crosslinked. As a consequence, the microcapsules can be used in a wide range of organic solvent based reactions.

The microcapsules containing the catalyst may be added to the reaction system to be catalysed and, following completion of the reaction, may be recovered for example by filtration. The recovered microcapsules may be returned to catalyse a further reaction and re-cycled as desired. Alternatively, the microcapsules containing the catalyst may be used as a stationary catalyst in a continuous reaction. For instance, the microcapsule particles could be immobilised with a porous support matrix (e.g. membrane). The microcapsule is permeable to the extent that catalysis may take place either by diffusion of the reaction medium through the polymer shell walls or by absorption of the reaction medium through the pore structure of the microcapsule.

Thus according to a further aspect of the present invention there is provided a process for the preparation of a microencapsulated catalyst which comprises (a) dissolving or dispersing the catalyst in a first phase,
(b) dispersing the first phase in a second, continuous phase to form an emulsion,
(c) reacting one or more microcapsule wall-forming materials at the interface between the dispersed first phase and the continuous second phase to form a microcapsule polymer shell encapsulating the dispersed first phase core and optionally
(d) recovering the microcapsules from the continuous phase.

Preferably the first phase is an organic phase and the second, continuous phase is an aqueous phase. Suitably a protective colloid (surfactant) is used to stabilise the emulsion.

If desired the recovered microcapsules may be washed with a suitable solvent to extract the first phase, and in particular the organic phase solvent from the core. A suitable solvent, usually water, may also be used to remove the protective colloid or surfactant.

The microcapsule wall-forming material may for example be a monomer, oligomer or pre-polymer and the polymerisation may take place in situ by polymerisation and/or curing of the wall-forming material at the interface. In the alternative polymerisation may take place at the interface by the bringing together of a first wall-forming material added through the continuous phase and a second wall-forming material in the discontinuous phase.

It will be appreciated that the microencapsulated catalyst of the present invention may be used for any reaction appropriate to that catalyst and that the scope of the present invention is not limited to use of the catalyst in any particular reaction type or reaction medium. In general however many of the reactions catalysed by transition metal catalysts take place in an organic solvent. Certain organic solvents may cause the microcapsule polymer to swell and this may aid contact of the reactants with the catalyst. Examples of the types of reactions in which it may be appropriate to use the microencapsulated catalyst of the present invention include Suzuki couplings, Heck reactions, Stille reactions, hydrogenations, allylic alkylations, Sharpless asymmetric dihydroxylation and reactions which are generally known which utilise palladium acetate as a catalyst, for instance, those reactions discussed in *Palladium Reagents and Catalysts*, Tsuji, J., Published by Wiley (Chichester) 1995; *Metal Catalysed Cross-Coupling Reactions*, Edited by Diederich, F., and Stang P. J., Published by Wiley-VCH (Weinham) 1998; *Comprehensive Organometallic Chemistry,* 2nd Ed., Farina V., Edited by Abel E. W., Stone F. G., and Wilkinson G., Published by Pergamon (London) 1995; Vol 12, p 161; and *Transition Metal Reagents and Catalysis*, Tsuji J., Published by Wiley (Chichester) 2000.

According to a further aspect of the present invention there is provided a process for the preparation of optionally substituted biphenyls which comprises reacting an optionally substituted aryl halide or halide equivalent with an optionally substituted aryl boronic acid or ester in the presence of a catalyst system comprising a catalyst microencapsulated within a permeable polymer microcapsule shell.

According to a further aspect of the present invention there is provided a process for the preparation of optionally substituted biphenyls which comprises reacting an optionally substituted aryl halide or halide equivalent with a tri-alkylaryltin in the presence of a catalyst system comprising a catalyst microencapsulated within a permeable polymer microcapsule shell.

Preferred catalyst systems for use in the above two processes are as described hereinbefore. Preferably, the microcapsule shell is formed by interfacial polymerisation. More preferably the catalyst is based on palladium, colloidal palladium or palladium acetate being most preferred.

The optionally substituted aryl halide includes an optionally substituted aryl iodides, bromides or chlorides. Optionally substituted aryl halide equivalents include optionally substituted aryl compounds having an OTf substituent (where $Tf=SO_2CF_3$), Preferred processes include the following:

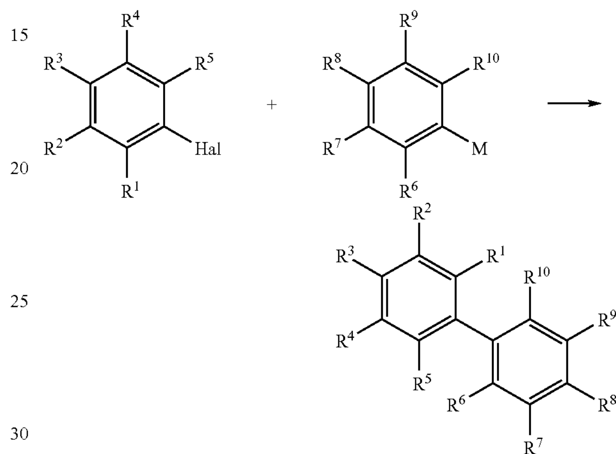

wherein:

Hal is a halide, preferably chloride, bromide or iodide, or a halide equivalent, preferably OTf;

$R^1$ to $R^{10}$ are each independently hydrogen or a substituent group; and

M is $B(OH)_2$, $B(OR^{11})_2$ or $Sn(R^{12})_3$ wherein $R^{11}$ is an alkyl or aryl group; and $R^{12}$ is an alkyl group.

When any of $R^1$ to $R^{10}$ are a substituent group, the group should be selected so as not to adversely affect the rate or selectivity of the reaction. Substituent groups include F, CN, $NO_2$, OH, $NH_2$, SH, CHO, $CO_2H$, acyl, hydrocarbyl, perhalogenated hydrocarbyl, heterocyclyl, hydrocarbyloxy, mono or di-hydrocarbylamino, hydrocarbylthio, esters, carbonates, amides, sulphonyl, sulphonamido and sulphonic acid ester groups wherein the hydrocarbyl groups include alkyl, and aryl groups, and any combination thereof, such as aralkyl and alkaryl, for example benzyl groups.

Alkyl groups which may be represented by $R^{1-10}$ include linear and branched alkyl groups comprising up to 20 carbon atoms, particularly from 1 to 7 carbon atoms and preferably from 1 to 5 carbon atoms. When the alkyl groups are branched, the groups often comprising up to 10 branch chain carbon atoms, preferably up to 4 branch chain atoms. In certain embodiments, the alkyl group may be cyclic, commonly comprising from 3 to 10 carbon atoms in the largest ring and optionally featuring one or more bridging rings. Examples of alkyl groups which may be represented by $R^{1-10}$ include methyl, ethyl, propyl, 2-propyl, butyl, 2-butyl, t-butyl and cyclohexyl groups.

Aryl groups which may be represented by $R^{1-10}$ may contain 1 ring or 2 or more fused rings which may include cycloalkyl, aryl or heterocyclic rings. Examples of aryl groups which may be represented by $R^{1-10}$ include phenyl, tolyl, fluorophenyl, chlorophenyl, bromophenyl, trifluoromethylphenyl, anisyl, naphthyl and ferrocenyl groups.

Perhalogenated hydrocarbyl groups which may be represented by $R^{1-10}$ independently include perhalogenated alkyl and aryl groups, and any combination thereof, such as aralkyl and alkaryl groups. Examples of perhalogenated alkyl groups which may be represented by $R^{1-10}$ include —$CF_3$ and —$C_2F_5$.

Heterocyclic groups which may be represented by $R^{1-10}$ independently include aromatic, saturated and partially unsaturated ring systems and may constitute 1 ring or 2 or more fused rings which may include cycloalkyl, aryl or heterocyclic rings. The heterocyclic group will contain at least one heterocyclic ring, the largest of which will commonly comprise from 3 to 7 ring atoms in which at least one atom is carbon and at least one atom is any of N, O, S or P. Examples of heterocyclic groups which may be represented by $R^{1-10}$ include pyridyl, pyrimidyl, pyrrolyl, thiophenyl, furanyl, indolyl, quinolyl, isoquinolyl, imidazoyl and triazoyl groups.

Preferably one or more of $R^1$, $R^5$, $R^6$ or $R^{10}$ is hydrogen. Most preferably at least three of $R^1$, $R^5$, $R^6$ or $R^{10}$ are hydrogen.

The processes may advantageously be used in the production of biphenyls where one or more of $R^2$, $R^4$, $R^7$ or $R^9$ are a cyano group.

According to a further aspect of the present invention there is provided a process for the preparation of optionally substituted alkenes which comprises reacting an optionally substituted aryl halide or halide equivalent with an alkene optionally substituted with up to three substituents in the presence of a catalyst system comprising a catalyst microencapsulated within a permeable polymer microcapsule shell.

Preferred catalyst systems for use in the above two processes are as described hereinbefore. Preferably, the microcapsule shell is formed by interfacial polymerisation. More preferably the catalyst is based on palladium, colloidal palladium or palladium acetate being most preferred.

The optionally substituted aryl halide includes an optionally substituted aryl iodides, bromides or chlorides. Optionally substituted aryl halide equivalents include optionally substituted aryl compounds having an OTf substituent (where Tf=$SO_2CF_3$).

Preferred processes include the following:

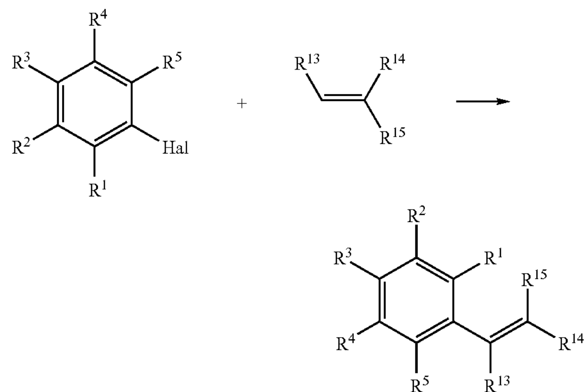

wherein:

Hal is a halide, preferably chloride, bromide or iodide, or a halide equivalent, preferably OTf;

$R^1$ to $R^5$ are each independently hydrogen or a substituent group; and $R^{13}$ to $R^{15}$ are each independently hydrogen or a substituent group.

When any of $R^1$ to $R^5$ are a substituent group, the group should be selected so as not to adversely affect the rate or selectivity of the reaction. Substituent groups include F, CN, $NO_2$, OH, $NH_2$, SH, CHO, $CO_2H$, acyl, hydrocarbyl, perhalogenated hydrocarbyl, heterocyclyl, hydrocarbyloxy, mono or di-hydrocarbylamino, hydrocarbylthio, esters, carbonates, amides, sulphonyl, sulphonamido and sulphonic acid ester groups wherein the hydrocarbyl groups include alkyl, and aryl groups, and any combination thereof, such as aralkyl and alkaryl, for example benzyl groups.

$R^{13}$ to $R^{15}$ are preferably selected from the substituent groups listed above for $R^1$. Optionally one or more of $R^{13}$&$R^{14}$ or $R^{14}$&$R^{15}$ may be joined to form an optionally substituted ring. When any of $R^{13}$&$R^{14}$ or $R^{14}$&$R^{15}$ are joined to form an optionally substituted ring, the ring preferably contains 5, 6 or 7 ring atoms which are preferably carbon atoms.

Most preferably, one or more of $R^{13}$ to $R^{15}$ are selected from CN, $NO_2$, acyl, ester hydrocarbyl, and hydrocarbyloxy groups.

According to a further aspect of the present invention there is provided a process for the preparation of diols which comprises reacting an olefin in the presence of a catalyst system comprising osmium tetroxide microencapsulated within a permeable polymer microcapsule shell.

Preferred processes include the following:

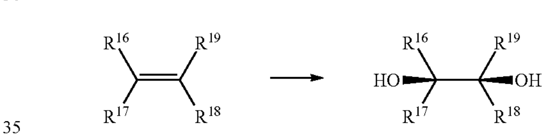

wherein:

$R^{16}$ to $R^{19}$ are each independently hydrogen or a substituent group.

Most preferably two or more of $R^{16}$ to $R^{19}$ are substituent groups.

When any of $R^{16}$ to $R^{19}$ are a substituent group, the group should be selected so as not to adversely affect the rate or selectivity of the reaction. Substituent groups include halide, CN, $NO_2$, OH, $NH_2$, SH, CHO, $CO_2H$, acyl, hydrocarbyl, perhalogenated hydrocarbyl, heterocyclyl, hydrocarbyloxy, mono or di-hydrocarbylamino, hydrocarbylthio, esters, carbonates, amides, sulphonyl, sulphonamido and sulphonic acid ester groups wherein the hydrocarbyl groups include alkyl, and aryl groups, and any combination thereof, such as aralkyl and alkaryl, for example benzyl groups.

Optionally one or more of $R^{16}$&$R^{17}$, $R^{17}$&$R^{18}$, $R^{18}$&$R^{19}$ or $R^{16}$&$R^{19}$ may be joined to form an optionally substituted ring. When any of $R^{16}$&$R^{17}$, $R^{17}$&$R^{18}$, $R^{18}$&$R^{19}$ or $R^{16}$&$R^{19}$ are joined to form an optionally substituted ring, the ring preferably contains 5, 6 or 7 ring atoms which are preferably carbon atoms.

According to a further aspect of the present invention there is provided a process for preparation of a hydrogenated product comprising reacting a substrate, wherein the substrate contains a hydrogenatable group or bond, with hydrogen in the presence of a catalyst system comprising a catalyst microencapsulated within a permeable polymer microcapsule shell.

Preferred catalyst systems for use in the above two processes are as described hereinbefore. Preferably, the microcapsule shell is formed by interfacial polymerisation. More preferably the catalyst is based on palladium, colloidal palladium or palladium acetate being most preferred.

Substrates which contain a hydrogenatable group or bond include organic compounds with carbon-carbon double or triple bonds, particularly optionally substituted alkenes or alkynes, and organic compounds substituted with groups such as nitro, nitroso, azido and other groups which are susceptible to reduction by hydrogen in the presence of a metal catalyst.

Advantageously, selective reduction of one type of hydrogenatable group or bond in the presence of other types of groups or bonds which are susceptible to reduction by hydrogen may be achieved by use of the catalyst systems of the present invention under appropriate conditions.

The invention is illustrated by the following examples. The use of the catalysts of the invention for catalysis of typical reactions is illustrated but the invention is not limited to the use of the catalysts for any specific reaction. In the following Examples GOSHENOL is polyvinyl alcohol, SOLVESSO 200 is just a high boiling (230-257° C.) mixture of aromatics (mainly naphthalenes), TERGITOL XD is the polyoxypropylene polyoxyethylene ether of butyl alcohol, REAX 100M is sodium lignosulfonate. REAX, TERGITOL and GOSHENOL are added as colloid stabilisers and detergents.

EXAMPLES

Example 1

This Example illustrates the encapsulation of $Pd(OAc)_2$ in a polyurea matrix. $Pd(OAc)_2$ (0.4 g Aldrich, 98%) was suspended in Solvesso 200 (5 g) and the solution stirred for 20 min. To this mixture, polymethylene polyphenylene di-isocyanate (PMPPI) (4 g) was added and stirred for a further 20 min. The mixture was then added to an aqueous mixture containing REAX 100 M (1.8 g), TERGITOL XD (0.3 g) and Poly Vinyl Alcohol (PVOH) (0.6 g) in deionised water (45 ml) while shearing (using a FISHER rotary flow impeller) at 1000 rpm for 1 minute. The micro-emulsion thus obtained was paddle-stirred at room temperature for 24 h. The microcapsules obtained were filtered though a polyethylene frit (20 micron porosity) and the capsules were washed in the following order: deionised water (10×50 ml), ethanol (10×50 ml), acetone (10×50 ml), dichloromethane (2×10 ml), hexane (3×50 ml), ether (1×50 ml), and dried. Typical loading of $Pd(OAc)_2$ in microcapsules was 0.12 mmol/g (based on Pd analysis).

Example 2

This Example illustrates an alternative procedure for encapsulation of $Pd(OAc)_2$ in a polyurea matrix. A mixture of $Pd(OAc)_2$ (5 g) and polylmethylene polyphenylene di-isocyanate (PMPPI, 50 g) in dichloroethane (70 mL) was stirred for 1 h at room temperature. The resulting dark solution was added at a steady rate to an aqueous mixture containing REAX 100 M (10 g), TERGITOL XD (2.5 g) and GOSHENOL (5 g) in de-ionised water (250 mL) while shearing (using a HEIDOLPH radial flow impeller, 50 mm) at 800 rpm for 2 minutes. The resulting oil-in-water emulsion was paddle-stirred (or shaker-stirred) at room temperature for 16 hours. Ethylene diamine (5 g) was added and the mixture paddle-stirred (or shaker-stirred) for 6 hours. The polyurea microcapsules obtained were filtered though a polyethylene frit (20-micron porosity) and were washed with de-ionised water, acetone, ethanol, ether and dried.

Example 3

This Example illustrates the encapsulation of colloidal palladium nanoparticles in a polyurea matrix.

Step 1: Preparation of Colloidal Palladium $Pd(OAc)_2$ (0.3 g, Aldrich 98%) and tetra-n-octylammonium bromide (1.46 g, 3 equiv., Aldrich 98%) were dissolved in dry tetrahydrofuran (250 ml) and refluxed for 5 hours under argon. The solvent was removed under reduced pressure to a volume of about 50 ml, and 20 g of SOLVESSO 200 was added and the excess tetrahydrofuran removed under reduced pressure.

Step 2: Encapsulation of Colloidal Palladium

PMPPI (9 g) was added to the above solution of Solvesso 200 containing colloidal palladium. The mixture was quickly added to an aqueous mixture containing REAX 100 M (1.8 g), TERGITOL XD (0.3 g) and PVOH (0.6 g) in deionised water (45 ml) while shearing (using a Fisher rotary flow impeller) at 1000 rpm for 1 minute The microemulsion thus obtained was paddle stirred at room temperature for 24 hours. The microcapsules were filtered though a polyethylene frit (20 micron porosity) and the capsules were washed in the following order: deionised water (10×50 ml), ethanol (10×50 ml), acetone (10×50 ml), dichloromethane (2×10 ml), hexane (3×50 ml), ether (1×50 ml), and dried.

Example 4

This Example illustrates the encapsulation of osmium tetroxide in a polyurea matrix.

PMPPI (3 g) was added to a solution of SOLVESSO 200 (3 g) containing osmium tetroxide (0.132 g). The resulting dark solution was added at a steady rate to an aqueous mixture containing REAX 100 M (0.6 g), TERGITOL XD (0.1 g) and polyvinyl alcohol (PVA) (0.29) in deionised water (15 ml) while shearing (using a Heidolph radial flow impeller, 30 mm) at 750 rpm for 1 minute. The resulting oil-in-water emulsion was paddle stirred (100 rpm) at room temperature for 48 hours. The polyurea microcapsules obtained were filtered though a polyethylene frit (20 micron porosity) and the capsules were washed in the following order: deionised water (10×50 ml), ethanol (10×50 ml), acetone (10×50 ml), hexane (3×50 ml), ether (1×50 ml) and dried.

Example 5

This Example gives a general procedure for Suzuki type reactions using encapsulated colloidal palladium nanoparticles.

To a solution of aryl bromide (or chloride) (1 mmol), boronic acid (1.5 mmol), sodium acetate (3 mmol) in toluene/water/ethanol (4:2:1, 7 ml) was added microencapsulated palladium (prepared as described in Example 3, 0.3 g, 5 mol %, assuming about 0.142 g of metallic palladium has been encapsulated in 9 g of polyurea) and the reaction mixture stirred at 80° C. for 6 hours. The reaction mixture was diluted with ether (25 ml) and filtered though a polyethylene frit (20 micron porosity). The filtrate was extracted with ether (2×20 ml) and the combined organic layers were washed with brine (20 ml) and dried ($MgSO_4$). Evaporation under reduced pressure and purification by column chromatography gave the products.

Example 6

This Example gives a general procedure for Suzuki type reactions using encapsulated palladium acetate. The procedure for encapsulated $Pd(OAc)_2$ was identical to that used for encapsulated colloidal palladium in Example 5, except potassium carbonate (3 mmol) was used in place of sodium acetate as base. Typical loading of $Pd(OAc)_2$ in microcapsules is 0.12 mmol/g (based on Pd analysis). Typically, 5 mol % of catalyst is added to the reaction.

The following compounds were prepared using this method and the encapsulated $Pd(OAc)_2$ catalysts prepared as described in Example Method 1:

4,4'-Dimethoxybiphenyl

From 4-methoxy-bromobenzene and 4-methoxyphenyl boronic acid, yield 87%; mp 178-180° C. (lit.,[1] 179-180° C.); IR: 1599, 1493, 1466 and 1290; $^{1}$H NMR (400 MHz; $CDCl_3$): 7.47 (4H, d, J 8.7), 6.96 (4H, d, J 8) and 3.84 (6H, s); $^{13}$C NMR ($CDCl_3$): 159.1, 133.9, 128.1, 114.5 and 55.7; m/z (EI) 214 (100%, M+), 171 (70), 128 (50) and 69 (40)(Found: $M^+$, 214.099. $C_{14}H_{14}O_2$ requires M, 214.099).

4'-Fluoro-4-methoxybiphenyl

From 4-fluoro-bromobenzene and 4-methoxyphenyl boronic acid, yield 89%; mp 92-94° C. (lit.,[2] 94-96° C.); IR: 1504, 1276 and 1041; $^{1}$H NMR (400 MHz; $CDCl_3$): 7.53-7.46 (4H, m), 7.11 (2H, t, J 8.7), 6.98 (2H, d, J 8.8) and 3.85 (3H, s); m/z (EI) 202 (95%, $M^+$), 159 (100), 133 (90) and 69 (40)(Found: $M^+$, 202.079. $C_{13}H_{11}FO$ requires M, 202.079).

4'-Nitro-4-methoxybiphenyl

From 4-nitro-bromobenzene and 4-methoxyphenyl boronic acid, yield 91%; mp 104-105° C. (lit.,[3] 106-107° C.); IR: 1597, 1509, 1342 and $^{125}$I; $^{1}$H NMR (600 MHz; $CDCl_3$): 8.27 (2H, d, J 9), 7.69 (2H, d, J 8.4), 7.58 (2H, d, J 9), 7.02 (2H, d, J 8.4) and 3.87 (3 H, s); $^{13}$C NMR ($CDCl_3$): 160.4, 147.1, 146.5, 131, 128.5, 127, 124.1, 114.6 and 55.4; m/z (EI) 229 (25%, $M^+$), 169. (30), 131 (30) and 69 (100)(Found: $M^+$, 229.073. $C_{13}H_{11}NO_3$ requires M, 184.074).

2,2'-Dimethoxybiphenyl

From 2-methoxy-bromobenzene and 2-methoxyphenyl boronic acid, yield 71%; mp 155-157° C. (lit.,[4] 155° C.); IR: 1590, 1501, 1481, 1455 and 1238; $^{1}$H NMR (400 MHz; $CDCl_3$): 7.34 (2H, m), 7.25 (2H, d, J 8), 7.02-6.97 (4H, m) and 3.77 (6H, s); $^{13}$C NMR ($CDCl_3$): 157, 131.4, 128.5, 127.8, 120.3, 111.1 and 55.6; m/z (EI) 214 (100%, $M^+$), 184 (50) and 69 (40)(Found: $M^+$, 214.099. $C_{12}H_{14}O_2$ requires M, 214.099).

4'-Methoxy-4-acetylbiphenyl

From 4-methoxy-bromobenzene and 4-acetylphenyl boronic acid, yield 84%; mp 150-151° C. (lit.,[5] 153-154° C.); IR: 1676, 1602, 1456 and 1236; $^{1}$H NMR (400 MHz; $CDCl_3$): 8.01 (2H, d, J 8.4), 7.64 (2H, d, J 8.3), 7.58 (2H, d, J 8.8), 7 (2H, d, J 8.5), 3.86 (3H, s) and 2.62 (3H, s); $^{13}$C NMR ($CDCl_3$): 197.6, 159.9, 145.3, 135.3, 132.2, 128.9, 128.3, 126.5, 114.4, 55.3 and 26.5; m/z (EI) 226 (80%, $M^+$), 211 (100) and 69 (60)(Found: $M^+$, 226.099. $C_{15}H_{14}O_2$ requires M, 226.099).

4'-Fluoro-4-acetylbiphenyl

From 4-fluoro-bromobenzene and 4-acetylyphenyl boronic acid, yield 90%; mp 109-110° C. (lit.,[6] 105-106° C.); IR: 1681, 1600, 1496, 1361 and 1255; $^{1}$H NMR (400 MHz; $CDCl_3$): 8.08 (2H, d, J 8.4), 7.65-7.57 (4H, m), 7.16 (2H, d, J 8.6) and 2.63 (3H, s); m/z (EI) 214 (80%, $M^+$), 199 (90), 170 (100) and 69 (50)(Found: $M^+$, 214.079. $C_{14}H_{11}FO$ requires M, 214.079).

4'-nitro-4-acetylbiphenyl

From 4-nitro-bromobenzene and 4-acetylphenyl boronic acid, yield 97%; mp 144-146° C. (lit.,[7] 150-151° C.); IR: 1681, 1530, 1497, 1361 and 1280; $^{1}$H NMR (400 MHz; $CDCl_3$): 8.02 (2H, d, J 8.5), 7.64-7.56 (4H, m), 7.16 (2H, t, J 8.5) and 2.63 (3H, s); $^{13}$C NMR ($CDCl_3$): 197.5, 164.2, 144.7, 136, 128.9, 127, 116, 115.7 and 26.6; m/z (EI) 199 (30%, $M^+-C_2H_2O$), 131 (50) and 69 (100)(Found: $M^+-C_2H_2O$, 199.062).

4-Methoxybiphenyl

From 4-methoxy-bromobenzene and phenyl boronic acid, yield 94%; mp 85-88° C. (lit.,[8] 90-91° C.); IR: 1604, 1582, 1520, 1486 and 1286; $^{1}$H NMR (400 MHz; $CDCl_3$): 7.57-7.52 (4H, m), 7.42 (2H, t, J 7.9), 7.31 (1H, t, J 7.3), 6.99 (2H, d, J 8.8) and 3.86 (3H, s); $^{13}$C NMR ($CDCl_3$): 159.1, 140.8, 133.8, 128.7, 128.1, 126.6, 115.7, 114.2 and 55.3; m/z (EI) 184 (100%, $M^+$), 141 (60) and 69 (40)(Found: $M^+$, 184.088. $C_{13}H_{12}O_2$ requires M, 184.088).

4-Fluorobiphenyl

From 4-fluoro-bromobenzene and phenyl boronic acid, yield 93%; mp 73-75° C. (lit.,[9] 73-75° C.); IR: 1599, 1519, 1487 and 1196; $^{1}$H NMR (400 MHz; $CDCl_3$): 7.56-7.53 (4H, m), 7.43 (2H, d, J 7.8), 7.34 (1H, t, J 8) and 7.15-7.1 (2H, m); rr/z (EI) 172 (70%, $M^+$), 119 (30) and 69 (100) (Found: $M^+$, 172.068. $C_{12}H_9F$ requires M, 172.068).

4-Nitrobiphenyl

From 4-nitro-bromobenzene and phenyl boronic acid, yield 97%; mp 110-113° C. (lit.,[8] 114-115° C.); IR: 1596, 1513, 1481, 1350 and 1236; $^{1}$H NMR (400 MHz; $CDCl_3$): 8.32-8.28 (2H, m), 7.76-7.72 (2H, m), 7.65-7.61 (2H, m) and 7.52-7.42 (3H, m); $^{13}$C NMR ($CDCl_3$): 147.6, 147.1, 138.7, 129.1, 128.8, 127.7, 127.3 and 124; m/z (EI) 199 (20%, $M^+$), 169(70), 131 (85) and 119 (100)(Found: $M^+$, 199.063. $C_{12}H_9NO_2$ requires M, 199.063).

Experiments have shown that the use of microwave reactors may enhance reaction rates and reactions yields in Suzuki coupling reactions using catalysts according to the present invention.

Example 7

The general procedure for Suzuki type reactions using encapsulated $Pd(OAc)_2$ was followed, but using toluene/water 20:1 as the solvent. This method allows more convenient work-up of the reactions after catalyst filtration. Similar yields of 4-nitrobiphenyl were obtained in test reactions.

Example 8

This Example illustrates a representative procedure for carbonylation reactions using encapsulated $Pd(OAc)_2$.

Preparation of butyl 4-methylbenzoate

Microencapsulated $Pd(OAc)_2$ (prepared as described in Example 1, 0.23 g, 2 mol %, based on palladium content) was added to a solution of 4-iodotoluene (1 mmol) and triethylamine (4 mmol) in 1,2-Dimethoxyethane/n-butanol (1:1, 10 mL). The reaction vessel was evacuated and purged with carbon monoxide (CO). The reaction mixture was stirred at 95° C. for 24 h under a CO atmosphere (using a balloon). The mixture was allowed to cool to room temperature, diluted with dichloromethane (50 mL) and filtered through a polyethylene frit (20-micron porosity). The filtrate was washed with water (2×20 mL) and dried ($MgSO_4$). Evaporation under reduced pressure and purification by column chromatography gave butyl 4-methylbenzoate, 89%; IR: 1714; $^1$H NMR (400 MHz; $CDCl_3$): 7.93 (2H, d, J 8.2), 7.23 (2H, d, J 8), 4.31 (2H, t, J 6.6), 2.41 (3H, s), 1.78-1.71 (2H, m), 1.49 (2H, sext, J 7.5) and 0.98 (3H, t, J 7.4); $^{13}$C NMR ($CDCl_3$): 167.2, 143.8, 130.0, 129.4, 128.2, 65.0, 31.2, 22.0, 19.7 and 14.1.

Example 9

This Example illustrates a representative procedure for Heck type reactions using encapsulated $Pd(OAc)_2$.

Preparation of butyl 4-nitro-trans-cinnamate

Microencapsulated $Pd(OAc)_2$ (prepared as described in Example 1, 0.25 g, 2 mol %, based on palladium content) was added to a solution of 4-bromo nitrobenzene (1 mmol), butyl acrylate (1.5 mmol) and ammonium acetate (3 mmol) in 1,2-dimethoxyethane (5 mL) and stirred at 90° C. for 8 h. The reaction mixture was cooled to room temperature, diluted with ether (50 mL) and filtered through a polyethylene frit (20-micron porosity). The filtrate was washed with water (2×20 mL), brine (20 mL) and dried ($MgSO_4$). Evaporation under reduced pressure and purification by column chromatography gave butyl 4-nitro-trans-cinnamate 87%; IR: 1709, 1643, 1519 and 1343; $^1$H NMR (400 MHz; $CDCl_3$): 8.24 (2H, d, J 8.8), 7.7 (1H, d, J 15.6), 7.67 (2H, d, J 8.5), 6.55 (1H, d, J 16.1), 4.23 (2H, t, J 7), 1.7 (2H, qn, J 7.6), 1.44 (2H, sext, J 7.6) and 0.97 (3H, t, J 7.4); $^{13}$C NMR ($CDCl_3$): 166.0, 148.4, 141.5, 140.6, 128.5, 124.1, 122.6, 64.8, 30.6, 19.1 and 13.6.

Example 10

In an alternative general procedure for Heck type reactions using encapsulated $Pd(OAc)_2$ the method of Example 9 was followed, but using isopropanol/toluene as the solvent and tetrabutylammonium acetate as base in place of ammonium acetate. This alternative solvent system provided similar yields to that of Example 9.

Example 11

This Example illustrates a representative procedure for Stille type reactions using encapsulated $Pd(OAc)_2$

Preparation of 4-nitrobiphenyl

Microencapsulated $Pd(OAc)_2$ (prepared as described in Example 1, 0.25 g, 2 mol %, based on palladium content) was added to a solution of 4-bromo nitrobenzene (1 mmol), trimethylphenyltin (1.5 mmol) and ammonium acetate (3 mmol) in 1,2-dimethoxyethane (5 mL) and stirred at 90° C. for 6 h. The reaction mixture was cooled to room temperature, diluted with ether (50 mL) and filtered through a polyethylene frit (20-micron porosity). The filtrate was washed with water (2×20 mL), brine (20 mL) and dried ($MgSO_4$). Evaporation under reduced pressure and purification by column chromatography gave 4-nitrobiphenyl, 90%: IR, $^1$H NMR and $^{13}$C NMR identical with sample obtained from the Suzuki reaction in Example 5.

Example 12

This Example illustrates an alternative general procedure for Stille type reactions using encapsulated $Pd(OAc)_2$. The procedure of Example 11 was used, but using isopropanol/toluene as the solvent and tetrabutylammonium acetate as base in place of ammonium acetate. Similar yields of 4-nitrobiphenyl were obtained.

Example 13

This Example illustrates a general procedure for cis-hydroxylation of olefins using encapsulated osmium tetroxide.

To a solution of olefin (1 mmol) and N-methylmorpholine N-oxide (NMO) (1.5 mmol), in acetone/water (10:1, 10 ml) was added microencapsulated osmium tetroxide (5 mol %, based on osmium content) and the reaction mixture stirred at room temperature for 12-24 h. The reaction mixture was diluted with acetone (25 ml) and filtered though a polyethylene frit (20 micron porosity). The filtrate was treated with a saturated solution of sodium metabisulfite (50 ml, stir for 30 min) and extracted with ethyl acetate (3×20 ml) and the combined organic layers were washed with brine (20 ml) and dried ($MgSO_4$). Evaporation under reduced pressure and purification by column chromatography gave the products.

The following compounds were prepared using this method:

1-Phenyl-1,2-propanediol

From trans-(1-phenyl)prop-1-ene, yield 80%; IR: 3321; $^1$H NMR (400 MHz; $CDCl_3$): 7.4-7.28 (5H, m), 4.35 (1H, d, J 7.3), 3.85 (1H, q, J 6.4), 2.9-2.6 (2H, br s) and 1.05 (3H, d, J 6.3); $^{13}$C NMR ($CDCl_3$): 141.0, 128.4, 128.1, 126.8, 79.4, 72.2 and 18.7.

1,2-Diphenyl-1,2-ethanediol

From trans-(1,2-diphenyl)ethene, yield 84%; IR: 3343; $^1$H NMR (400 MHz; $CDCl_3$): 7.33-7.12 (10H, m), 4.66 (2H, s) and 2.84 (2H, s); $^{13}$C NMR ($CDCl_3$): 134.6, 122.9, 122.7, 121.7 and 73.8.

2-Phenyl-1,2-propanediol

From 2-phenylprop-1-ene, yield 90%; IR: 3348; $^1$H NMR (400 MHz; $CDCl_3$): 7.46 (2H, d, J 7.9), 7.37 (2H, J 7.6), 7.28 (1H, t, J 7.1), 3.79 (1H, d, J 11), 3.63 (1H, d, J 11), 2.58 (1H, br s), 1.8 (1H, br s) and 1.54 (3H, s); $^{13}$C NMR ($CDCl_3$): 144.9, 128.4, 127.1, 125.0, 74.8, 71.0 and 26.0.

5,6-Decanediol

From trans-dec-5-ene, yield 85%; IR: 3376; $^1$H NMR (400 MHz; $CDCl_3$): 3.43-3.38 (2H, m), 2.01 (2H, d, J 4.1), 1.51-1.25 (12H, m), 0.91 (6H, t, J 7.2); $^{13}$C NMR ($CDCl_3$): 74.5, 33.3, 27.8, 22.7 and 13.9.

2-Methyl-1-phenyl-1,2-propanediol

From 2-methyl-1-phenylprop-1-ene, yield 83%; IR: 3382; $^1$H NMR (400 MHz; $CDCl_3$): 7.39-7.2 (5H, m), 4.43 (1H, d, J 2.1), 3.56 (1H, d, J 2.6), 2.87 (1H, br s), 1.15 (3H, s) and 1.04 (3H, s); $^{13}$C NMR ($CDCl_3$): 140.7, 127.8, 127.6, 127.5, 80.7, 73.5, 26.4 and 23.4.

1-Phenyl-1,2-cyclohexanediol

From 1-phenylcyclohexene, yield 82%; IR: 3402; $^1$H NMR (400 MHz; $CDCl_3$): 7.59-7.2 (5H, m), 4.0 (1H, dt, J 10.9 and 4), 2.57 (1H, d, J 1.7), 2.02-1.01 (9H, m); $^{13}$C NMR ($CDCl_3$): 146.3, 128.4, 127.0, 125.1, 75.7, 74.5, 38.5, 29, 2, 24.3 and 21.0.

2,3-Dihydroxy-3-phenyl methylpropionate

85%; IR: 3396 and 1733; $^1$H NMR (400 MHz; $CDCl_3$): 7.42-7.19 (5H, m), 5.02 (1H, dd, J 7 and 2.7), 4.38 (1 h, dd, J 5.7 and 2.9), 3.82 (3H, s), 3.08 (1H, d, J 5.9) and 2.70 (1H, d, J 7.1); $^{13}$C NMR ($CDCl_3$): 173.1, 139.9, 128.4, 126.1, 75.6, 74.7, 74.4 and 52.8.

1-Benzyloxy-1,5,6-hexanetriol

73%; IR: 3348; $^1$H NMR (400 MHz; $CDCl_3$): 7.36-7.24 (5H, m), 4.48 (2H, s), 3.85 (2H, br s), 3.63 (1H, m), 3.54 (1H, dd, J 11.2 and 2.6), 3.47 (2H, t, J 6.4), 3.35 (1H, dd, J 11.1 and 7.69) and 1.69-1.35 (6H, m); $^{13}$C NMR ($CDCl_3$): 138.8, 128.8, 128.0, 127.9, 73.3, 72.4, 70.6, 67.0, 33.2, 30.0 and 22.6; m/z (ESI) (Found: M+Na 247.1305. $C_{13}H_{20}O_3Na$ requires 247.1305).

Example 14

This Example illustrates the recycle of microencapsulated $Pd(OAc_2)$ catalyst in the preparation of 4-Nitrobiphenyl.

4-Nitro-bromobenzene and phenyl boronic acid were reacted as described in Example 6. The catalyst was recovered by filtration, washed and dried (as described in Example 1). This process was then repeated 4 times with fresh reagents and the recycled catalyst. The yields of isolated 4-Nitrobiphenyl were as follows:

| | |
|---|---|
| Reaction (1) | 97% |
| Reaction (2) | 90% |
| Reaction (3) | 92% |
| Reaction (4) | 94% |
| Reaction (5) | 93%. |

Example 15

This Example illustrates the recycle of microencapsulated OsO4 in the preparation of 1-Phenyl-1,2-propanediol.

Trans-(1-phenyl)prop-1-ene was reacted with encapsulated $OsO_4$ as described in Example 13. The catalyst was recovered by filtration, washed and dried (as described in Example 4). This process was then repeated 4 times with fresh reagents and the recycled catalyst. The yields of isolated 1-Phenyl-1,2-propanediol were as follows:

| | |
|---|---|
| Reaction (1) | 77% |
| Reaction (2) | 79% |
| Reaction (3) | 76% |
| Reaction (4) | 73% |
| Reaction (5) | 79%. |

Example 16

In a similar experiment to that of Example 15 above, encapsulated $OsO_4$ was recycled and used to prepare 6 different products in turn with the yields indicated in parenthesis:

| | |
|---|---|
| 1-Phenyl-1,2-propanediol | (74%) |
| 1,2-Diphenyl-1,2-ethanediol | (86%) |
| 2-Phenyl-1,2-propanediol | (88%) |
| 5,6-Decanediol | (83%) |
| 2-Methyl-1-phenyl-1,2-propanediol | (77%) |
| 1-Phenyl-1,2-cyclohexanediol | (88%) |

When used after storage for several months without any special precautions (such as an inert atmosphere), the microcapsules were just as effective in these oxidations.

Qualitative leach test experiments were carried out by stirring the microcapsules in solution for 24 h. The microcapsules were filtered off and the remaining solution was tested in attempted catalytic osmylation experiments. The results of the tests on the solutions showed that no reaction occurred, which suggests that there was no appreciable leaching of osmium from the encapsulated catalyst system.

Example 17

In an experiment to compare the performance of a microencapsulated palladium catalyst with other palladium catalysts in which the palladium is either immobilised by conventional means or is present as palladium acetate, the following reaction was repeated employing several catalysts systems:

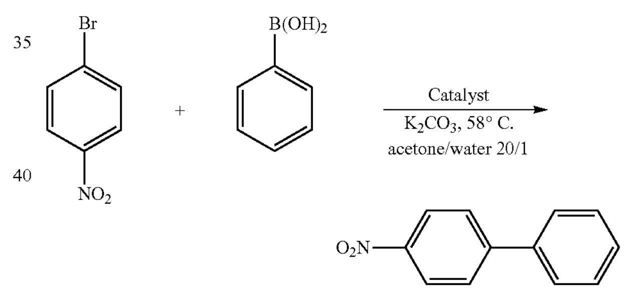

In each case the conversion was measured after four hours reaction to establish catalyst reactivity:

| Catalyst | Reaction Time | % Yield |
|---|---|---|
| Encapsulated Pd (ex Example 27) | 4 h | 50% |
| Pd on Polymer (ex Aldrich) | 4 h | 7% |
| Pd on Carbon | 4 h | 23% |
| Pd Black | 4 h | 4% |
| $PdOAc_2$ (non immobilised) | 4 h | 15% |

Conclusion: the Encapsulated Pd (a catalyst system according to the present invention) demonstrates higher activity/reactivity compared to conventional palladium catalyst systems.

Example 18

In an experiment designed to probe potential solvent effects on the reaction rates of a microencapsulated palladium catalyst, the following reaction was carried out in various solvents systems using 12 mol % of 0.4 mmol/g encapsulated Pd as prepared in Example 27, 1.5 equiv of phenyl boronic acid and 3 equiv of potassium carbonate, and heating at 80° C.:

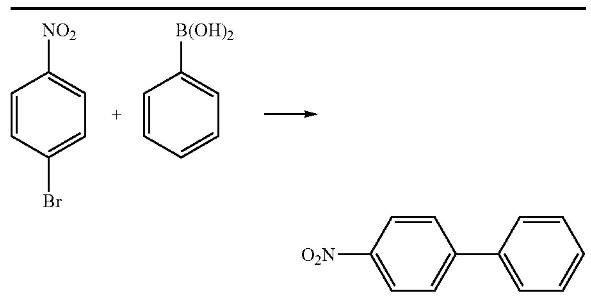

| Solvent | Solvent Ratio | Reaction Time (hours) | Yield (%) |
|---|---|---|---|
| Acetone/Water | 20/1 | 1 | 100 |
| IMS/Water | 20/1 | 0.7 | 94 |
| Diglyme/Water | 20/1 | 3 | 99 |
| Acetonitrile/Water | 20/1 | 3 | 95 |
| THF/Water | 20/1 | 5 | 93 |
| DMA/Water | 20/1 | 4 | 91 |
| Butanone/Water | 20/1 | 4.7 | 91 |

Conclusion: the microencapsulated palladium catalyst of the present invention demonstrate high efficacy in a range of solvent systems.

Example 19

In an experiment to determine whether there was potential leaching of Pd from a microencapsulated palladium catalyst of the present invention (as prepared in Example 27), ICP analysis of crude reaction mixtures from a Suzuki coupling reaction carried out in the presence of different solvent types was carried out:

| Solvent | Pd leached (%) |
|---|---|
| Toluene/water/ethanol (4/2/1) | 0.1 |
| Toluene/water (20/1) | <0.1 |
| Acetone/water (20/1) | 0.14 to 2 |
| THF/water (20/1) | 0.05 |
| IMS/water (20/1) | 0.02 |
| DME/water(20/1) | 0.1 |
| Butanone/water (20/1) | 0.4 |
| Acetonitrile/water (20/1) | 0.1 |
| Diglyme/water (20/1) | 0.01 |

Conclusion: the low percentage leaching values obtained demonstrate that the microencapsulated catalyst system is quite resistant to the leaching effects in a range of solvents.

Example 20

A palladium microencapsulated catalyst system of the present invention was subjected to physical inspection and testing.

By optical microscope the microcapsules were observed to have a spherical to oval appearance which in some part appeared to be influenced by the catalyst loading. Low palladium loadings producing more predominantly spherical microcapsules, high palladium loadings producing more predominantly oval microcapsules.

Scanning electron microscopy (SEM) on sectioned microcapsules has shown a homogeneous microporous structure. The energy dispersive x-ray (EDX) pattern on cross sections of the microcapsules showed a homogeneous distribution of Pd throughout cross-sectional area. Similarly, the transmission electron micrograph (TEM) of a sliced microcapsule shows an even distribution of palladium.

The encapsulated palladium acetate catalyst systems are air-stable under typical storage temperatures and no special storage precautions are required. Samples stored at room temperature have not shown any loss in activity over a 6-month period. DSC and other thermal stability tests have shown no self heating on warming samples to 400° C. in air atmosphere.

Initial results suggest that the Pd microcapsules are physically stable under typical agitation conditions. A suspension of Pd microcapsules in toluene was stirred for 5 weeks by magnetic follower, the level of Pd in the toluene was found to be constant at 0.5 ppm over that period.

The particle size distribution for a batch was determined by Coulter Counter using an LS Particle Size Analyser. A typical particle size trace for a Pd microcapsule batch which has been classified to remove fines of less than 50 microns and large particles of greater than 300 microns is shown in FIG. 1.

| Calculations from 0.375 μm to 2000 μm | | | | | |
|---|---|---|---|---|---|
| Volume: | 100% | | | | |
| Mean: | 175.512 μm | | S.D: | 48.60 μm | |
| Median: | 174.3 μm | | C.V.: | 27.7% | |
| D(3, 2): | 133.6 μm | | Skewness: | −0.106 Left skewed | |
| Mode: | 185.4 μm | | Kurosis: | 0.314 Leptokurtic | |
| %< | 10 | 25 | 50 | 75 | 90 |
| μm | 117.4 | 143.9 | 174.3 | 207.9 | 239.6 |

Example 21

A series of hydrogenation reaction have been carried out using an encapsulated palladium catalyst. All reactions were carried out using 2 mmol alkene, 250 mg or 5 mol % immobilised palladium acetate as prepared according to Example 27 below, 25 bar hydrogen, in 10 ml ethanol solvent, stirring in an autoclave at room temperature for 18 hours. All reactions proceeded to 100% conversion.

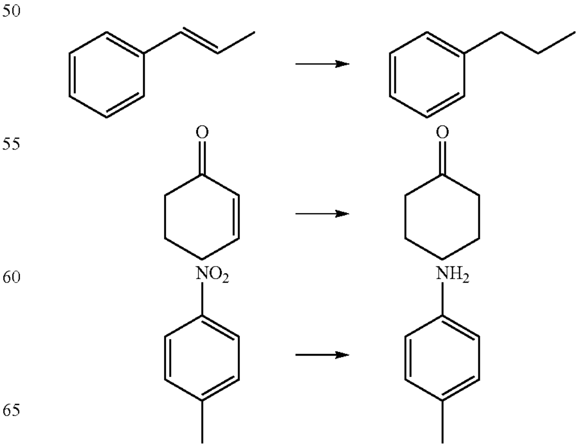

-continued

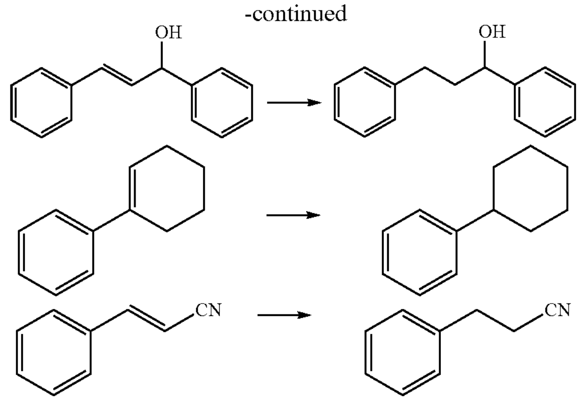

Example 22

The following reaction was carried out using 2 mmol alkene, 250 mg or 5 mol % (based on metal content) immobilised palladium acetate as prepared according to Example 27, 25 bar hydrogen, in 10 ml isopropanol/ethylacetate solvent, stirring in an autoclave at room temperature for 18 hours.

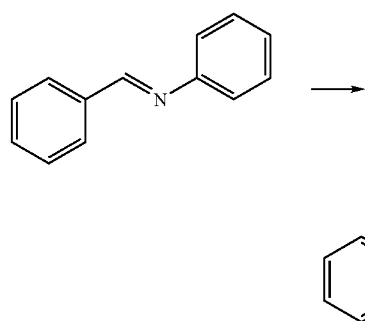

71%

Example 23

The following reaction was carried out using 2 mmol alkene, 250 mg or 5 mol % (based on metal content) immobilised palladium acetate as prepared according to Example 27, 25 bar hydrogen, in 10 ml ethanol/ethylacetate solvent, stirring in an autoclave at room temperature for 18 hours.

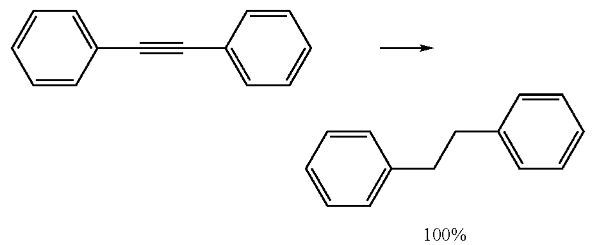

100%

Example 24

The following hydrogenations were all performed utilising a simplified laboratory technique wherein a hydrogen atmosphere is maintained in a reaction flask by means of a hydrogen balloon attached to the reaction flask. All reactions were carried out on 2 mmol alkene with 250 mg or 5 mol % (based on metal content) immobilised palladium acetate as prepared according to Example 27, in 10 ml ethanol solvent, stirring at room temperature for 48 hours.

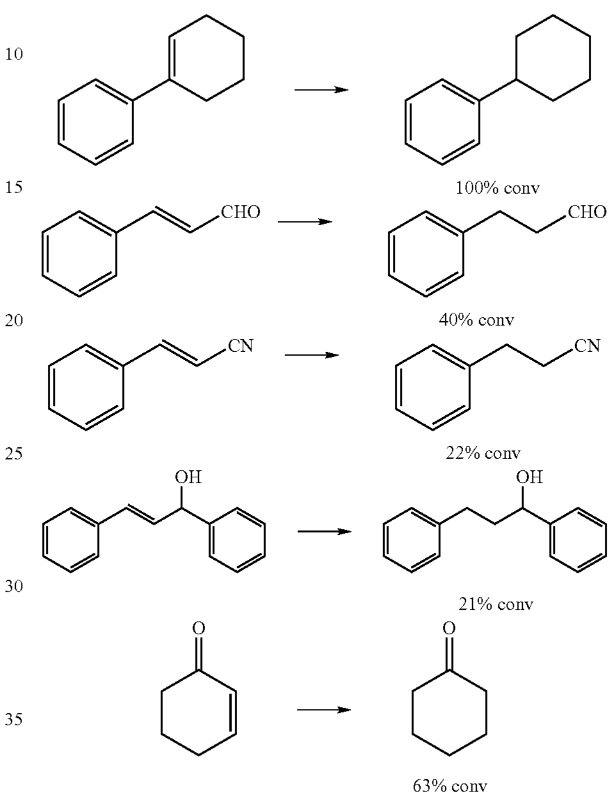

Conclusion, that while the microencapsulated Pd acetate works well in hydrogenation of olefins with complete conversion at 25 bar, in some cases good conversion is also obtained under conditions where the simple use of a hydrogen balloon for extended periods was employed.

Example 25

The following reaction was carried out using 1 mmol alkene, 0.5 mol % (based on metal content) microencapsulated palladium acetate (0.4 mmol/g Pd) as prepared according to Example 27 below, hydrogen balloon, room temperature. Various reaction conditions are compared which show that it may be advantageous to pre-activate the catalyst.

| Run | Reaction Conditions | Conversion after 5 hours (%)[a] | Conversion after 18 hours (%)[a] |
|---|---|---|---|
| 1 | EtOH (5 ml) | 13 | 63 |
| 2 | EtOH/EtOAc 1/1 (5 ml) | 2 | 51 |

-continued

| Run | Reaction Conditions | Conversion after 5 hours (%)[a] | Conversion after 18 hours (%)[a] |
|---|---|---|---|
| 3 | EtOH (5 ml)/AcOH (0.05 ml) | 3 | 41 |
| 4 | EtOH (5 ml), activated Pd[b] | 35 | 100 |
| 5 | EtOH (5 ml), activated Pd[c] | 97 | 100 (after 6 hours) |

[a] conversion was detected by GC

[b] the microencapsulated palladium acetate was activated by stirring in ethanol under hydrogen atmosphere (18 hours at 25 bar)

[c] used recovered microencapsulated palladium from Run 4

Example 26

An encapsulated palladium acetate catalysed addition of the sodium salt of diethyl malonate to 1,3-diphenylprop-2-enyl acetate was studied out under the following conditions: 5 mol % (based on metal content) microencapsulated palladium acetate (0.4 mmol/g Pd) as prepared according to Example 27, 20 mol % ligand, reflux.

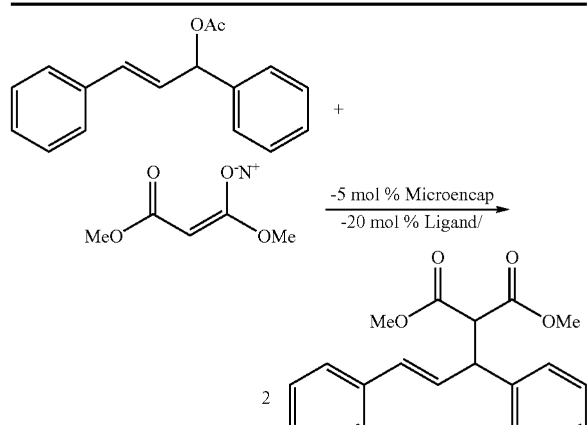

| Experiment | Solvent | Ligand | Reaction Time/hr | Catalyst Recovery/% | Product Yield/% |
|---|---|---|---|---|---|
| A | THF | $PPh_3$ | 47 | 98 | 76 (isolated Yield) |
| B | Dioxane | $PPh_3$ | 21 | 95 | Quantitative (HPLC) |

The acetate starting material for the above Examples was synthesised using the following procedure.

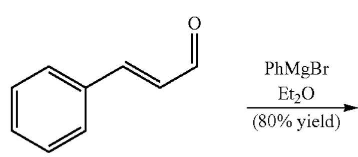

-continued

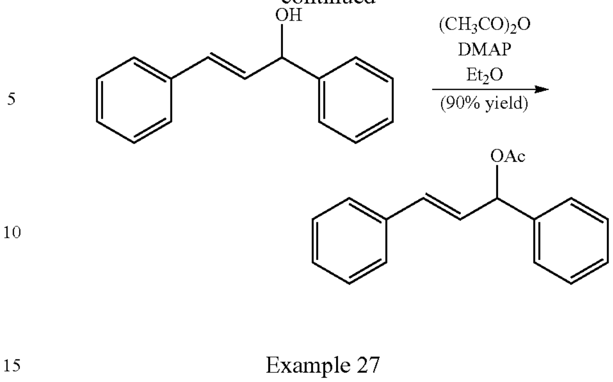

Example 27

Method of preparation of the catalysts system used in EXAMPLES 21-26.

Preparation of the Oil Phase:

$Pd(OAc)_2$ (29.5 g) was dissolved in chloroform (257.1 g, Aldrich) and to the resulting solution PMPPI (191.1 g, Aldrich) was added. The mixture was then allowed to stir on rollers for 2 hours at room temperature.

Encapsulation of Palladium:

The aqueous mixture containing deionised water (803 g), 40% Reax 100M solution (95.5 g), 25% PVOH solution (76.4 g) and 20% Tergitol XD solution (47.7 g) was stirred at 16° C. using a 3-blade turbine stirrer. The oil phase was added at a steady stream and the oil-in-water emulsion sheared at 275 rpm for 12 minutes. The shear rate was then reduced to 200 rpm. At the onset of polymerisation process few drops of defoamer (DREWPLUS S4382, Ashland) were added to disperse the foam on the surface of the microemulsion. The mixture was then allowed to stir at room temperature for 24 hours. The microcapsules were then filtered through a glass sinter funnel (porosity 1645 micron) and washed with deionised water (5×600 ml), ethanol (3×600 ml) and hexane (2×600 ml). The resulting capsules were then dried in a vacuum oven at 50° C. for 4 hours.

Analytical Results:

| | |
|---|---|
| Yield of Pd EnCat: | 185 g |
| ICP-AES analysis: | 4.2% Pd Loading: 0.40 $mmolg^{-1}$ |
| Particle size distribution: | 140 μm (average) |
| Moisture content: | 1.3% |

Example 28

This Example illustrates a method to remove pendent amine groups from the polyurea wall material of the microencapsulated $Pd(OAc)_2$ In a 10 ml reaction vessel phenylisocyanate (0.3 g) was dissolved in dimethoxy ethane (8 ml). Microencapsules (1 g) containing $Pd(OAc)_2$ at a loading of 0.4 mmol/g was then added and the resulting mixture stirred at room temperature for 2 hours. The microcapsules were then filtered and washed with DME repeatedly (5×10 ml) before being dried at 50° C. under vac.

Example 29

The encapsulated osmium tetroxide has also been shown to work in asymmetric dihyroxylations. In contrast to the conventional Sharpless conditions referred to in Chemical Reviews 1994, 94, 2483-2547, the preferred solvent is THF/ water 1/1. Thus, 5 mol % (based on metal content) of the encapsulated osmium tetroxide microparticles described in Example 4, was used in reactions carried out at room temperature in THF/water 1/1 for 20 to 36 hours under the following conditions:

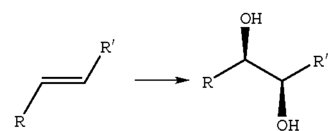

Ligand is (DHQD)2PHAL hydroquinidine2,5-diphenyl-1,4-phthalazinediyl diether Potassium ferricyanide (III), methanesulphonamide The Table below summarises the yields and enantiomeric excesses for a series of asymmetric dihydroxylation experiments following the conditions described above:

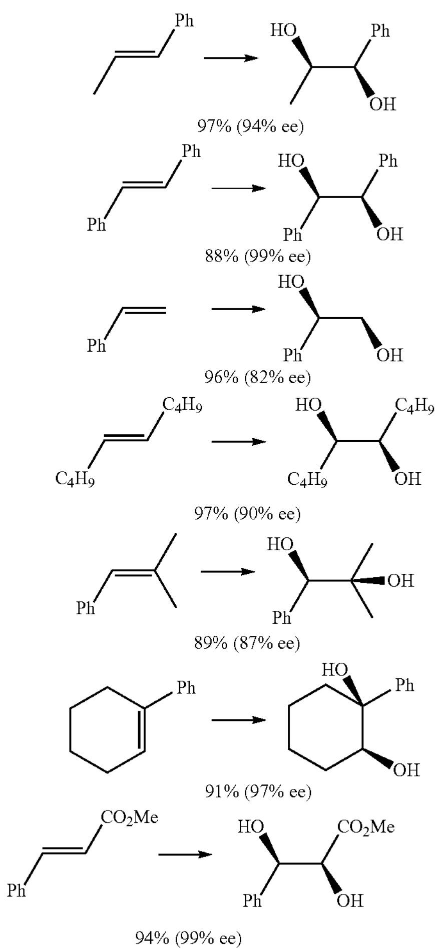

Example 30

A combination of microencapsulated osmium tetroxide and periodate was found to be very effective in the cleavage of olefins to yield aldehydes in high yield. Thus, a series of reactions were carried out at room temperature using 5 mol % (based on metal content) of the encapsulated osmium tetroxide microparticles described in Example 4 in an THF/water (1:1) and sodium periodate as the co-oxidant.

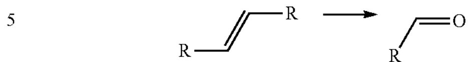

The following oxidation was repeated five time under the same conditions but using recovered (recycled) catalyst with greater than 95% yield in each case:

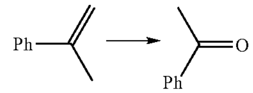

The invention claimed is:

1. A reusable catalyst system comprising a transition metal catalyst based on a transition metal selected from the group consisting of platinum, palladium, ruthenium, and rhodium, within a porous polymeric matrix bead wherein the porous polymeric matrix bead is formed by an interfacial polymerization process comprising (a) dissolving or dispersing the transition metal catalyst in a first phase;

(b) dispersing the first phase in a second continuous phase to form an emulsion;

(c) reacting one or more bead-forming materials at the interface between the dispersed first phase and the continuous second phase to form a porous polymeric matrix bead encapsulating the dispersed first phase transition metal catalyst; and optionally (d) recovering a porous polymeric matrix bead from the continuous phase;

wherein the bead-forming materials comprise at least one aromatic polyisocyanate with or without at least one tolylene diisocyanate, wherein the porous polymeric matrix bead has a homogeneous porous structure and the catalyst is homogeneously distributed throughout the porous polymeric matrix bead, and the catalyst is coordinated with polymer of the porous polymeric matrix bead, whereby the catalyst is maintained within the bead for catalytic contact with organic liquid which enter the porous polymeric matrix bead.

2. The catalyst system according to claim 1 wherein the at least one aromatic polyisocyanate and/or tolylene diisocyanate is selected from the group consisting of 1-chloro-2,4-phenylene diisocyanate, m-phenylene diisocyanate (and its hydrogenated derivative), p-phenylene diisocyanate (and its hydrogenated derivative), 4,4'-methylenebis(phenyl isocyanate), 2,4-tolylene diisocyanate, tolylene diisocyanate (60% 2,4-isomer, 40% 2,6-isomer), 2,6-tolylene diisocyanate, 3,3'-dimethyl-4,4'-biphenylene diisocyanate, 4,4'-methylenebis (2-methylphenyl isocyanate), 3,3'-dimethoxy-4,4'-biphenylene diisocyanate, 2,2',5,5'-tetramethyl-4,4'-biphenylene diisocyanate, 80% 2,4- and 20% 2,6-isomer of tolylene diisocyanate, polymethylene polyphenylisocyanate (PMPPI), tetramethylxylene diisocyanate and 1,5-naphthylene diisocyanate.

3. The catalyst system according to claim 1 wherein the transition metal catalyst is selected from the group consisting of metal oxide catalysts, metal diphosphine catalysts, metal phosphine catalysts, metal phosphoramidate catalysts, metal aminophosphine catalysts, metal arylamine catalysts, metal diamine catalysts, metal aminoalcohol catalysts, metal phosphate catalysts, metal salt catalysts, metal alkoxide catalysts, metal arene catalysts, metal arene phosphine catalysts, metal carbene catalysts, and metallocycle catalysts.

4. The catalyst system according to claim 1 wherein the catalyst is selected from the group consisting of colloidal palladium and palladium acetate.

5. A process for the preparation of the catalyst system of claim 1 which comprises forming a porous polymeric bead around the transition metal catalyst to be microencapsulated by interfacial polymerisation, wherein the interfacial polymerisation comprises condensation of at least one aromatic polyisocyanate with or without at least one tolylene diisocyanate.

6. The process according to claim 5 wherein the at least one polyisocyanate and/or tolylene diisocyanate is selected from the group consisting of 1-chloro-2,4-phenylene diisocyanate, m-phenylene diisocyanate (and its hydrogenated derivative), p-phenylene diisocyanate (and its hydrogenated derivative), 4,4'-methylenebis(phenyl isocyanate), 2,4-tolylene diisocyanate, tolylene diisocyanate (60% 2,4-isomer, 40% 2,6-isomer), 2,6-tolylene diisocyanate, 3,3'-dimethyl-4,4'-biphenylene diisocyanate, 4,4'-methylenebis(2-methylphenyl isocyanate), 3,3'-dimethoxy-4,4'-biphenylene diisocyanate, 2,2',5,5'-tetramethyl-4,4'-biphenylene diisocyanate, 80% 2,4- and 20% 2,6-isomer of tolylene diisocyanate, polymethylene polyphenylisocyanate (PMPPI), and 1,5-naphthylene diisocyanate.

7. The process according to claim 5 or claim 6 wherein a crosslinking reagent is present.

8. The process according to claim 5 wherein unreacted amine groups are converted to urea, amide or urethane groups by post reaction with a monoisocyanate, acid chloride or chloroformate.

9. A process for the preparation of the catalyst system of claim 1 which comprises (a) dissolving or dispersing the transition metal catalyst in a first phase;

(b) dispersing the first phase in a second continuous phase to form an emulsion;

(c) reacting one or more bead-forming materials at the interface between the dispersed first phase and the continuous second phase to form a porous polymeric bead encapsulating the dispersed first phase transition metal catalyst; and optionally (d) recovering porous polymeric beads from the continuous phase;

wherein the bead-forming materials comprise at least one aromatic polyisocyanate with or without at least one tolylene diisocyanate.

10. The process according to claim 9 wherein the at least one aromatic polyisocyanate and/or tolylene diisocyanate is selected from the group consisting of 1-chloro-2,4-phenylene diisocyanate, m-phenylene diisocyanate (and its hydrogenated derivative), p-phenylene diisocyanate (and its hydrogenated derivative), 4,4'-methylenebis(phenyl isocyanate), 2,4-tolylene diisocyanate, tolylene diisocyanate (60% 2,4-isomer, 40% 2,6-isomer), 2,6-tolylene diisocyanate, 3,3'-dimethyl-4,4'-biphenylene diisocyanate, 4,4'-methylenebis(2-methylphenyl isocyanate), 3,3'-dimethoxy-4,4'-biphenylene diisocyanate, 2,2',5,5'-tetramethyl-4,4'-biphenylene diisocyanate, 80% 2,4- and 20% 2,6-isomer of tolylene diisocyanate, polymethylene polyphenylisocyanate (PMPPI), tetramethylxylene diisocyanate and 1,5-naphthylene diisocyanate.

11. The process according to claim 9 wherein the wall-forming materials comprise a crosslinking reagent.

12. The process according to claim 9 wherein the transition metal catalyst is based on palladium.

13. The process according to claim 12 wherein the catalyst is selected from the group consisting of colloidal palladium and palladium acetate.

14. A process for the preparation of optionally substituted biphenyls which comprises reacting an optionally substituted aryl halide or halide equivalent with an optionally substituted aryl boronic acid or ester in the presence of a catalyst system according to claim 1.

15. A process for the preparation of optionally substituted biphenyls which comprises reacting an optionally substituted aryl halide or halide equivalent with a tri-alkylaryltin in the presence of a catalyst system according to claim 1.

16. A process for the preparation of optionally substituted alkenes which comprises reacting an optionally substituted aryl halide or halide equivalent with an alkene optionally substituted with up to three substituents in the presence a catalyst system according to claim 1.

17. A process for the preparation of a hydrogenated product which comprises reacting a substrate, wherein the substrate contains a hydrogenatable group or bond, with hydrogen in the presence of a catalyst system according to claim 1.

18. The process according to claim 17 wherein the catalyst is selected from the group consisting of colloidal palladium and palladium acetate.

* * * * *